(12) United States Patent
Coffman et al.

(10) Patent No.: US 7,855,280 B2
(45) Date of Patent: Dec. 21, 2010

(54) SEPARATION METHODS

(75) Inventors: Jonathan L. Coffman, Hampstead, NH (US); Russell I. Shpritzer, Tewksbury, MA (US); Steven M. Vicik, Boxborough, MA (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/518,532

(22) Filed: Sep. 8, 2006

(65) Prior Publication Data

US 2007/0066806 A1 Mar. 22, 2007

Related U.S. Application Data

(60) Provisional application No. 60/717,838, filed on Sep. 15, 2005.

(51) Int. Cl.
*A23J 3/20* (2006.01)
*C07K 14/00* (2006.01)

(52) U.S. Cl. .......................................... 530/412; 514/2
(58) Field of Classification Search ....................... None
See application file for complete search history.

(56) References Cited

U.S. PATENT DOCUMENTS

| 3,607,857 | A | * | 9/1971 | Nelson | 530/389.6 |
|---|---|---|---|---|---|
| 3,657,071 | A | | 4/1972 | Bergmeyer et al. | |
| 3,874,999 | A | * | 4/1975 | Zaremba et al. | 435/239 |
| 3,974,134 | A | * | 8/1976 | Sternberg | 530/420 |
| 4,197,238 | A | * | 4/1980 | Murata et al. | 530/364 |
| 5,429,746 | A | * | 7/1995 | Shadle et al. | 210/635 |
| 2001/0034066 | A1 | | 10/2001 | Alam | |

FOREIGN PATENT DOCUMENTS

| EP | 0574050 | 12/1993 |
|---|---|---|
| WO | WO96/38469 | 12/1996 |

OTHER PUBLICATIONS

Pratima Bajpai, et al., "Clarification of bacterial broth containing high a-amylase activity", *Journal Biotechnology Techniques*, vol. 4, No. 4, pp. 227-232 (1990).

* cited by examiner

*Primary Examiner*—Anand U Desai
(74) *Attorney, Agent, or Firm*—Margo H. Furman

(57) ABSTRACT

Separation methods, for example, to isolate a recombinant protein, are disclosed. In some implementations, a method includes forming a solid containing a first cation and a first anion in a medium containing a protein, and separating the solid from the protein.

69 Claims, 3 Drawing Sheets

SEPARATION METHODS

CROSS REFERENCE TO RELATED APPLICATIONS

This application claims the benefit of U.S. Provisional Application No. 60/717,838, filed on Sep. 15, 2005, which is incorporated herein by reference in its entirety.

TECHNICAL FIELD

The invention relates to separation methods, for example, methods of recovering a purified product from a fluid including impurities such as one or more soluble impurities, cells, cellular debris, or insoluble impurities.

BACKGROUND

Within the biotechnology industry, the purification of proteins on a commercial scale is an important challenge to the development of recombinant proteins for therapeutic and diagnostic purposes. Problems related to yield, purity, and throughput challenge the manufacturing sector. With the advent of recombinant protein technology, a protein of interest can be produced using cultured eukaryotic host cell lines engineered to express a gene encoding the protein. What can result from a host cell culturing process, however, is a mixture of the desired protein along with impurities that are either derived from the protein itself, such as protein variants, or from the host cell, such as host cell proteins, DNA, and cellular debris. The use of the desired recombinant protein for pharmaceutical applications may be contingent on being able to reliably recover adequate levels of the protein from these impurities. Recombinant technology can also produce proteins that are not found in nature, for example, novel mutant proteins, fusion proteins, or proteins with heterologous signal sequences that direct the secretion of the protein to the medium. Recombinant proteins can be expressed in many eukaryotic cell types, including Chinese Hamster Ovarian cells (CHO), baby hamster kidney (BHK), NS0 myeloma cells, and *Pichia pastoris* yeast cells.

Typically, to produce a recombinant protein, a recombinant DNA vector is created that contains a gene that codes for the protein to be expressed with appropriate sequences to direct the transcription and translation of the gene in the desired cell type. The vector can also contain sequences such as selectable or counterselectable markers, for example, drug resistance genes, and/or sequences designed to promote the stable retention of the protein expression sequences. For mammalian cells, plasmid and viral vectors, for example, retroviral vectors, can be used.

Following the creation of the vector, the vector is then introduced into the cells. The vector can be transfected as naked DNA using standard methods, for example, lipofection, calcium phosphate, DEAE-dextran, electroporation, or biolistics (gene gun). Viral vectors can be introduced by infection with viral particles. The cells are then screened or selected for those that contain the vector.

Cells that contain the vector and express the recombinant protein can be grown in a liquid medium or on a solid support, and the protein isolated from the cell culture. Mammalian cell density ranges between $10^6$ cells/mL to $2 \times 10^7$ cells per mL or more. Most proteins are secreted. Secreted protein concentrations can range between 4 mg/L to 10 g/L. However, if the protein is produced intracellularly, the cells are broken to release the protein, whereas if the protein is secreted, it can be isolated from the growth medium or the support following removal of the cells and cell debris. The isolated protein can then be purified.

Conventional biopharmaceutical protein purification methods used to remove cells and cellular debris include centrifugation, microfiltration, and depth filters. Filter aids, such as diatomaceous earth, can be used to enhance performance of these steps, but they are not always effective and sometimes significantly bind the product of interest. Their use may also require the addition of a solid or a homogeneous suspension that can be challenging as part of large-sale biopharmaceutical operations.

Polymeric flocculants can be used to aid in the clarification of mammalian cell culture process streams, but they can have limitations. For example, protamine sulfate preparations typically used as processing aids are limited in application due to concerns about inactivation of the protein of interest or product loss due to precipitation (Scopes, 1987). High quality reagent, such as that sold for medical use, can be expensive. In certain instances, removal to very low levels may require validation to ensure there are no unexpected effects in patients. For example, chitosan is not a well-defined reagent and there are concerns about its consistent performance in routine use in clarification applications. Multiple charged polymers, such as DEAE dextran, acrylamide-based polymers often used in waste-water treatment (NALCO Water Handbook, Chapter 8) and polyethylene amine (PEI) have been considered for use in clarification applications. With respect to the latter two types of polymers, the acrylamide reagents have the potential for contamination with toxic reagents and polyethylene amine, while a highly effective clarification reagent, is often contaminated with varying amounts of ethylenimine monomer, a suspected cancer agent (Scawen et al). Moreover, many of these polymers, including PEI, tend to bind almost irreversibly to many chromatography resins, thereby limiting downstream processing options. The regulatory and raw material reuse concerns associated with these polymers have limited their application primarily to academic studies.

Non-polymer based flocculants, such as alum and iron salts, have been utilized in the wastewater treatment industry (NALCO Water Handbook). These substances may appear to be non-useful in processing protein products, because they may bind to the protein product or may catalyze chemical reactions resulting in modifications of the protein that could affect safety or efficacy.

SUMMARY

The invention relates to separation methods. The separation methods can be used to isolate a protein, such as a recombinant protein, from a fluid containing impurities such as one or more soluble impurities, insoluble impurities, cells, or cellular debris.

In one aspect, the invention features separation methods that include the addition to a fluid one or more (e.g., two or more) soluble solutions that can form a precipitate that aids in the removal of impurities. The precipitate may associate more strongly with impurities and less strongly to a target product. The solution(s) can include soluble cations, e.g., metal ions and/or soluble anions that are capable of interacting with, e.g., particulates, colloidal material, cellular debris or cells, and form an insoluble precipitate, e.g., when mixed together. The resulting precipitate can be clarified or removed using solid-liquid separation techniques, such as microfiltration, depth filtration, or centrifugation. The treated fluid can have a reduced impurity level in comparison to untreated fluid processed similarly.

Impurities may be related to those elements found in suspension within the fluid. In some embodiments, the impurities include colloidal material, particulate material, cells, cell debris such as membrane fragments, and other large cellular complexes that are insoluble under typical processing conditions. Impurities may also refer to cellular components that remain soluble under typical processing conditions. DNA, host cell proteins and phospholipids are examples of cell components that are present in solution during clarification. Additionally, soluble product-related impurities, such as inactive isoforms or aggregated species may be present.

Impurity levels can be assessed by a variety of methods. One method, which provides a measure of the amount of debris in the fluid, is the nephalometric measurement of turbidity. Alternatively, the level of debris can be evaluated by measuring the area of membrane filter required to process a known volume of the fluid. Specific impurities may also be soluble in the fluid requiring specific biochemical tests to evaluate. DNA levels may be measured using fluorometric-based methods, such as by using the commercially available dye Picogreen (Invitrogen, Product Number P-7581). Alternate approaches include hybridization methods, such as slot-blot techniques, or polymerase chain reaction (PCR methods). Host cell protein levels may be evaluated by sodium dodecyl sulfate polyacrylamide gel electrophoresis (SDS-PAGE), reversed phase chromatography, or enzyme linked immunosorbent assay (ELISA) methods. Phospholipids may be analyzed by thin layer chromatography or high performance liquid chromatography.

The resulting precipitate can interact with both impurities in suspension and soluble impurities and this interaction can decrease the levels of these impurities in the purified fluid. As a result, the separation methods can provide cost, and/or time savings, as well as increased quality of product, for example, for an industrial process that uses mammalian cell culture for the production of recombinant proteins.

In another aspect, the invention features an increase in the performance of subsequent chromatographic steps, for example, the performance of a Protein A chromatographic step. Protein A chromatography is typically performed by direct application of cell-free conditioned medium to resin on which *Staphylococcus aureus* protein A has been immobilized. The resin is subsequently washed with an aqueous solution of neutral pH (approximately pH 6-8) and bound protein is often eluted with an acidic buffer. Prior to subsequent processing, the eluate pool is adjusted to neutral pH. The Protein A eluate pool often precipitates upon neutralization, especially when high density cell cultures are used for the load. In accordance with the invention, host cell protein removal by the Protein A step is greater when the load has been treated with a metal and an anion in comparison to an untreated fluid. In embodiments, the precipitation of the Protein A peak upon neutralization is often less when the load fluid has been treated with a cation and an anion providing a processing improvement.

In another aspect, the invention features selection of two soluble agents that, when mixed, form a solid that may improve process fluid purity with high product recovery under appropriate conditions. These agents may include, but are not limited to, calcium, manganese, magnesium, aluminum, cobalt, nickel, carbonate, fluoride, sulfite, phosphate, silicate and alginates. These compounds represent a combination of multivalent metal ions, with monovalent anions, or alternatively, multivalent or polyvalent anions, that are the preferred ligands to the metal. Salts of these cations and anions, when mixed under appropriate conditions potentially to form complexes that are sparingly soluble, may have utility in clarification applications.

In another aspect, the invention features a method, including forming a solid having a first cation and a first anion in a medium including a protein; and separating the solid from the protein.

In another aspect, the invention features a method, including introducing a first cation and a first anion into a medium having a protein; precipitating a solid having the first cation and the first anion; and separating the solid from the protein.

The methods described herein can be used to facilitate the filtration of one or more impurities from a medium, e.g., a fluid medium (e.g., a turbid suspension). For example, these methods can be used in a medium having one or more turbidity-causing agents that render the impurities difficult or inconvenient to remove using conventional filtration methods. Thus, in another aspect, the invention features a method that includes (i) forming a solid that includes a first cation and a first anion in a medium (e.g., a fluid medium) that includes a target moiety (e.g., a moiety to be purified) and one or more turbidity-causing agents such as precipitated or aggregated host cell proteins, lipids, cellular debris, whole cells, precipitated DNA, or the precipitate that forms upon the neutralization of the Protein A peak and (ii) separating the solid and the turbidity-causing agent(s) from the solution by, e.g., filtration. In embodiments, the turbidity causing agent can be of non-cellular origin, such as colloidal material, particulate material derived from environmental sources such as sand, dirt, ground stainless steel fines, or precipitated excipients such as antifoam or urea. The medium (e.g., a turbid suspension) can have a relatively high turbidity, such as greater than 5NTU as measured by a turbidity meter, or greater than 100NTU, or greater than 500NTU. In some embodiments, the presence of the solid can increase the filter capacity of the medium. In some embodiments, the turbidity of the treated medium (e.g., the medium after performing steps (i) and (ii)) can be less than the untreated medium. In some embodiments, the target moiety can be a protein (e.g., a soluble protein, e.g., an antibody). The method can further include recovering the target moiety from the solution after filtration.

Embodiments can include one or more of the following features.

The first cation can be calcium, magnesium, strontium, aluminum, scandium, lanthanum, silicon, titanium, zirconium, thorium, manganese, cobalt, copper, chromium, iron, nickel, zinc, or vanadium. The first cation can be calcium.

The first anion can be phosphate, carbonate, chromate, tungstate, hydroxide, halide, succinate, tartrate, citrate, sulfite, molybdate, nitrate, fluoride, silicate, and alginate. The first anion can be phosphate.

The first cation can be calcium and the first anion can be phosphate.

The solid can have a solubility product constant of no more than about $10^{-4}$ $M^2$.

The method can further include introducing from about 4 mM to about 200 mM of the first cation or the first anion into the medium.

The product of the concentrations of the first cation and the first anion can be greater than about $10^{-5}M^2$, $10^{-4}M^2$, or $2.7 \times 10^{-2}M^2$.

The concentrations of the first cation and the first anion in the medium can be different.

The concentrations of the first cation and the first anion in the medium can be substantially the same.

The method can further include changing the pH of the medium.

The pH of the medium can be maintained between from about 5 to about 9.

The method can provide separation of at least about 50% of the protein in the medium. The method can provide separation of at least about 70% of the protein in the medium.

The method can further include decreasing the clarified turbidity of the clarified medium by at least about 30% relative to a second clarified medium identical to the medium and free of the solid. The method can further include decreasing the turbidity of the clarified medium by at least about 50% relative to a second clarified medium identical to the medium and free of the solid.

The medium can include cells. The medium can further include mammalian cells. The medium can further include eukaryotic cells.

The method can further include centrifuging the medium, filtering the medium through a microfiltration membrane, or filtering the medium through a depth filter.

The solid can further include a second cation species or a second anion.

The medium that includes the protein, after the solid is formed and separated, can be applied to a Protein A column and eluted to provide an eluted peak having a lower turbidity than a similarly eluted peak of a second medium identical to the first medium and free of formation of the solid.

The medium that includes the protein, after the solid is formed and separated, can be applied to a Protein A column and eluted to provide an eluted peak having a lower soluble impurity level than an eluted peak of a second medium identical to the first medium and free of formation of the solid.

The first cation and the first anion can be introduced sequentially.

The first cation and the first anion can be introduced simultaneously.

The method can include introducing different concentrations of the first cation and the first anion into the medium or introducing the same concentration of the first cation and the first anion into the medium.

The method can further include adjusting the temperature of the medium.

The protein can be a secreted protein. The protein can be an antibody, an antigen-binding fragment of an antibody, a soluble receptor, a receptor fusion, a cytokine, a growth factor, an enzyme, or a clotting factor.

In embodiments where the protein is an antibody or a fragment thereof, it can include at least one, and typically two full-length heavy chains, and/or at least one, and typically two light chains. Alternatively, the antibodies or fragments thereof can include only an antigen-binding fragment (e.g., an Fab, F(ab')$_2$, Fv or a single chain Fv fragment). The antibody or fragment thereof can be a monoclonal or single specificity antibody. The antibody or fragment thereof can also be a human, humanized, chimeric, CDR-grafted, or in vitro generated antibody. In yet other embodiments, the antibody has a heavy chain constant region chosen from, e.g., IgG1, IgG2, IgG3, or IgG4. In another embodiment, the antibody has a light chain chosen from, e.g., kappa or lambda. In one embodiment, the constant region is altered, e.g., mutated, to modify the properties of the antibody (e.g., to increase or decrease one or more of: Fc receptor binding, antibody glycosylation, the number of cysteine residues, effector cell function, or complement function). Typically, the antibody or fragment thereof specifically binds to a predetermined antigen, e.g., an antigen associated with a disorder, e.g., a neurodegenerative, metabolic, inflammatory, autoimmune and/or a malignant disorder. Exemplary antibodies that can be separated by the methods of the invention include, but are not limited to, antibodies against an Aβ peptide, interleukin-13 (IL-13), interleukin-22 (IL-22), 5T4, and growth and differentiation factor-8 (GDF-8).

Other aspects, features and advantages will be apparent from the description of the preferred implementations thereof and from the claims.

DETAILED DESCRIPTION

Figure 1:
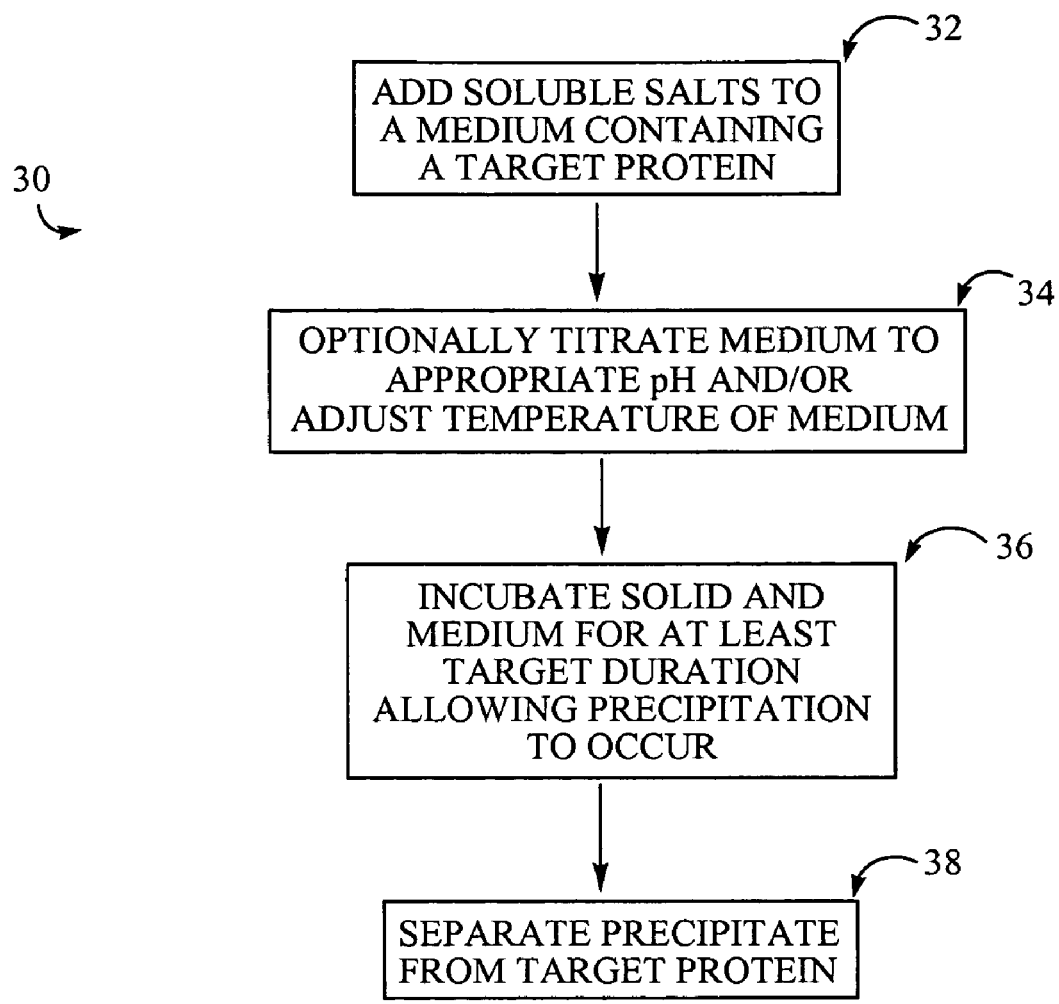
FIG. 1 is a flowchart of an embodiment of a separation method.

Referring to the FIG. 1, a method 30 for separating a targeted protein, such as a recombinant protein, is shown. Method 30 includes adding soluble salts (such as a calcium-containing salt and a phosphate-containing salt) to a fluid containing the protein (step 32), and impurities (which can include, but are not limited to, cellular debris, cells, DNA, host cell protein, and product related impurities such as inactive isoforms or aggregated species). The salt solutions can contain buffering agents to minimize pH changes or to optimize pH in the fluid upon mixing the salt solutions. Upon contact (e.g., mixing), the soluble salts often begin reacting to form an insoluble precipitate (such as solid calcium phosphate) that may settle in the medium. As shown in the FIG. 1, the medium may subsequently be titrated to a predetermined pH and the temperature adjusted (step 34), as necessary, to enhance precipitation. The settling precipitate also settles the cells and the debris, and potentially other impurities, while the target protein remains essentially soluble in the fluid. The fluid suspension is incubated under appropriate conditions for a target duration in order to promote precipitation and optimize clarification while maintaining high levels of target protein recovery (Step 36). Subsequently, the precipitate is separated from the fluid containing the target protein (step 38). This operation can occur in a variety of ways including gravity settling, centrifugation or filtration where filtration alternatives include tangential flow filtration, depth filtration, filtration through charged media, pad filtration where diatomaceous earth is a component of the media. The amount of cation and anion added to the media may not be sufficient to allow gravity settling of the precipitation or of debris but may still facilitate filtration by acting as a filter aid. The solid-liquid separation may include processing by a series of the aforementioned options, typically culminating with passage of the fluid through a filter with a low nominal pore-size rating (such as 0.45, 0.2 or 0.1 μM), which may be considered sterilizing in grade. The fluid clarified by the flocculation methods described herein may require less filtration area, either as part of the primary clarification or after an initial solid-liquid separation step such as centrifugation. Moreover, the turbidity of post pad and post-sterilizing grade filter can be significantly reduced compared to a non-flocculated control.

Typically, subsequent purification can proceed through a series of chromatographic steps, though other purification methods, such as crystallization and precipitation, can be conceived. After clarification using the described method, performance of the first chromatographic step, which for antibodies is often a Protein A column, may be enhanced. The overall removal of host cell-derived impurities, including host cell protein, can be greater than when flocculation treatment is not conducted. In many instances, neutralized Protein A eluate pool peak also has less precipitation as compared to the untreated control. This decreased level of precipitation may require less filter area or may reduce the needed processing time. The decreased level of precipitation also indicates the removal of an undesired impurity.

Without wishing to be bound by theory, it is believed that the insoluble precipitate enhances separation of the protein by selectively associating with the cells, cellular debris, and other process stream impurities while not significantly interacting with the protein. A non-limiting example of the hypothesized impurity removal process is shown in equation (1) below:

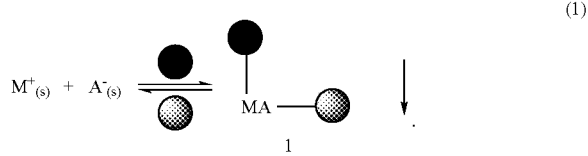

(1)

Referring to equation (1), $M^+$ is a soluble [i.e., "(s)"] cation, and $A-$ is soluble anion that can interact with $M^+$ to form an insoluble salt or complex; the shaded and filled circles each represent a soluble or insoluble impurity; 1 is an insoluble precipitate that includes the cation-anion salt or complex and impurities associated therewith (1 is sometimes referred to herein as the "final complex or salt" or "solid having a first cation and a first anion"); and the downward pointing arrow indicates that 1 is in precipitated form. For example, calcium phosphate can interact ionically and/or by chelation with DNA, host cell protein, and cellular debris, while not significantly interacting with the target protein. This selectivity allows the protein to remain in the supernatant, and subsequently, to be readily separated from the medium and other components of the conditioned medium.

Still referring to FIG. 1, separation method 30 includes introducing a first soluble salt and a second soluble salt into a medium (step 32). The medium can be, for example, a conditioned aqueous solution in which a recombinant protein has been formed. The first soluble salt includes a first cation, and the second soluble salt includes a first anion. Upon contact, the first cation and the first anion are capable of interacting in the medium and may begin to form an insoluble precipitate. The fluid environment may be adjusted at any time in pH or temperature to optimize precipitation conditions (e.g., step 34) and the solution is incubated for a target duration to allow the system to fully equilibrate (step 36).

In general, any cation (e.g., a first cation)/anion (e.g., a first anion) combination can be selected that is capable of forming a relatively insoluble salt or complex in the fluid containing the product of interest. In embodiments, such salts or complexes can be identified as being insoluble, sparingly soluble, practically insoluble, very slightly soluble, or slightly soluble in a solution comparable to the fluid containing the product of interest. Exemplary cation/anion combinations include those in which the selected cation (e.g., a first cation, e.g., $M^+$ in equation 2 below) and the selected anion (e.g., a first anion, e.g., $A^-$ in equation 2 below) are capable of forming a salt or complex (e.g., MA in equation 2 below) that is relatively insoluble in water:

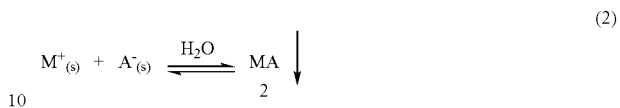

(2)

in which "(s)" and the downward pointing arrow are as defined with respect to equation (1). In many instances, characterization of solubility in water as described in *The Merck Index* or the *Handbook of Physics and Chemistry* or other similar references serves as an appropriate indicator of potential performance.

In some embodiments, the selected cation and the selected anion are capable of forming a salt or complex having a solubility product constant ($K_{sp}$) in water of from about $1 \times 10^{-50} M^2$ to about $1 \times 10^{-4} M^2$ (e.g., from about $1 \times 10^{-50} M^2$ to about $1 \times 10^{-5} M^2$, from about $1 \times 10^{-50} M^2$ to about $1 \times 10^{-6} M^2$, from about $1 \times 10^{-40} M^2$ to about $1 \times 10^{-4} M^2$. In some embodiments, exemplary cations and anions can be identified as a solubility product constant ($K_{sp}$) between the first cation and the first anion ([cation]×[anion]) of less than about $10^{-4} M^2$, for example, and preferably below about $10^{-5} M^2$ or $10^{-6} M^2$. Substances with $K_{sp}$ values of less than $10^{-4} M^2$ can be utilized in the methods since these substances, upon mixing the a cation and the anion can result in a final solution of at most 10 mM of each; addition of the cation or anion in excess of 10 mM can result in precipitation and subsequent flocculation. Substances with higher $K_{sp}$ values than those listed above can be used, however, an excessive amount of cation and anion can be needed to form the solid.

The cation (e.g., a first cation) can be an alkaline earth metal, a transition metal, or a main group element. These elements can be classified into hard acids, borderline acids, or soft acids. Examples of first cations include calcium ($Ca^{2+}$), magnesium ($Mg^{2+}$), strontium ($Sr^{2+}$), aluminum ($Al^{3+}$), copper (Cu(I) or Cu(II)), scandium ($Sc^{+3}$), lanthanum ($La^{+3}$), silicon ($Si^{4+}$), titanium (Ti(III) or Ti(IV)), thorium, zirconium, manganese (Mn(II) or Mn(III)), cobalt (Co(II) or Co(III)), chromium (Cr(II) or Cr(III)), iron (Fe(II) or Fe(III)), nickel ($Ni^{2+}$), zinc ($Zn^{2+}$), and vanadium (V(III), V(IV), or V(V)). These represent the hard and borderline acids. The first anion can be an atomic species or a molecular species. In some embodiments, the first cation can be $Ca^{2+}$, $Mg^{2+}$, Mn(II), Co(II), or $Ni^{2+}$. In certain embodiments, the first cation can be $Ca^{2+}$.

Examples of first anions include anions that are the preferred ligands to the metal ion used. For the hard acid and borderline acids, the anions may include fluoride, phosphate, carbonate, silicate, chromate, tungstate, hydroxide, sulfite, nitrate, molybdate, succinate, tartrate, and citrate, and to some extent sulfates and perchlorates (see *Aquatic Chemistry*, Editors W. Stumm and J S Morgan, J Wiley, (1981), p 343; and R. G. Pearson, *J. Amer. Chem. Soc.*, v 85, p 3533 (1963).) In some embodiments, the first anion can be phosphate, sulfite, carbonate, fluoride, molybdate, or silicate. In certain embodiments, the first anion can be phosphate.

In some embodiments, the first cation can be $Ca^{2+}$, and the first anion can be phosphate, sulfite, carbonate, fluoride, molybdate, or silicate. In certain embodiments, the first cation can be $Ca^{2+}$, and the first anion can be phosphate.

In some embodiments, the first cation can be $Mg^{2+}$, Mn(II), Co(II), or $Ni^{2+}$, and the first anion can be phosphate, carbonate, or fluoride.

The initial concentration for each of the first cation and the first anion (i.e., the concentration of the first cation and the first anion that is introduced into the medium (before the start of precipitation)) can range from about 2 millimolar to about 200 millimolar (e.g., from about 3 millimolar to about 200 millimolar, from about 4 millimolar to about 200 millimolar, from about 5 millimolar to about 200 millimolar, from about 4 millimolar to about 100 millimolar, from about 4 millimolar to about 50 millimolar, from about 4 millimolar to about 40 millimolar, from about 4 millimolar to about 30 millimolar, from about 4 millimolar to about 10 millimolar, from about 10 millimolar to about 80 millimolar, from about 10 millimolar to about 40 millimolar, from about 10 millimolar to about 30 millimolar, from about 20 millimolar to about 80 millimolar, from about 20 millimolar to about 40 millimolar, e.g., about 4 millimolar, about 6 millimolar, about 10 millimolar, about 13.3 millimolar, about 16 millimolar, about 20 millimolar, about 24 millimolar, about 30 millimolar, about 33.3 millimolar, about 40 millimolar, about 50 millimolar, or about 80 millimolar) depending upon the solubility of the final complex. In certain embodiments, the concentration of the first cation introduced into the medium (before the start of precipitation) can be about 6 millimolar, about 10 millimolar, about 20 millimolar, about 24 millimolar, about 30 millimolar, about 40 millimolar, about 50 millimolar, or about 80 millimolar. In certain embodiments, the concentration of the first anion introduced into the medium (before the start of precipitation) can be 4 millimolar, about 10 millimolar, about 13.3 millimolar, about 16 millimolar, about 20 millimolar, about 24 millimolar, about 30 millimolar, about 40 millimolar, about 50 millimolar, or about 80 millimolar. For example, the concentration of the first cation introduced into the medium (before the start of precipitation) can be about 30 millimolar, and the concentration of the first anion introduced into the medium (before the start of precipitation) can be about 20 millimolar. As another example, the concentration of the first cation introduced into the medium (before the start of precipitation) can be about 24 millimolar, and the concentration of the first anion introduced into the medium (before the start of precipitation) can be about 16 millimolar.

In some embodiments, the product of the above-described initial concentrations of the first cation and the first anion can be from about $4 \times 10^{-6}$ $M^2$ to about $4 \times 10^{-2}$ $M^2$ (e.g., from about $1.6 \times 10^{-5}$ $M^2$ to about $4 \times 10^{-2}$ $M^2$, from about $2.5 \times 10^{-5}$ $M^2$ to about $4 \times 10^{-2}$ $M^2$, from about $1.6 \times 10^{-5}$ $M^2$ to about $6.4 \times 10^{-3}$ $M^2$, or from about $2.5 \times 10^{-5}$ $M^2$ to about $6.4 \times 10^{-3}$ $M^2$. In some embodiments, the product of the above-described initial concentrations of the first cation and the first anion can be greater than about $1 \times 10^{-5} M^2$, greater than about $2 \times 10^{-5} M^2$, greater than about $1 \times 10^{-4} M^2$, greater than about $2 \times 10^{-4} M^2$, greater than about $10 \times 10^{-4}$ $M^2$, or greater than about $2.7 \times 10^{-2} M^2$. In some embodiments, these concentrations can result in significant precipitation of the insoluble salt together with the impurities. Concentrations that are too high may result in solid volume of greater than about 10% of the total fluid volume. Concentrations in excess of 500 mM cation or anion with low solubility constants may give large solids volume. Adequate product recovery from a large solid volume may be difficult using standard solid-liquid separation techniques. Examples of precipitates include calcium phosphate, calcium sulfite, calcium carbonate, calcium fluoride, calcium silicate, calcium molybdate, magnesium carbonate, magnesium phosphate, magnesium fluoride, manganese phosphate, manganese carbonate, cobalt phosphate, nickel phosphate, and nickel carbonate.

In some embodiments, the $K_{sp}$ of the final salt or complex in the fluid media (e.g., 1 in equation (1), i.e., the insoluble precipitate that includes the cation-anion salt or complex and impurities associated therewith) can be from about $1 \times 10^{-50}$ $M^2$ to about $1 \times 10^{-4}$ $M^2$ (e.g., from about $1 \times 10^{-50}$ $M^2$ to about $1 \times 10^{-5}$ $M^2$, from about $1 \times 10^{-50}$ $M^2$ to about $1 \times 10^{-6}$ $M^2$, from about $1 \times 10^{-40}$ $M^2$ to about $1 \times 10^{-4}$ $M^2$. In some embodiments, the $K_{sp}$ of the final salt or complex in the fluid media can be less than about $10^{-4}$ $M^2$, for example, and preferably less than about $10^{-5} M^2$ or $10^{-6} M^2$. For example, in the anti-IL13 #2 sample with 40 mM calcium and 20 mM phosphate in Table 1, the supernatant after centrifugation (i.e., after precipitation) contained 8.19 mM calcium and 1.04 mM phosphate. This level of soluble calcium and phosphate corresponds to a $K_{sp}$ of $8.5 \times 10^{-6}$ $M^2$. In the anti-AB #1 sample with 80 mM calcium and 20 mM phosphate in Table 1, the supernatant after centrifugation contained 22.2 mM calcium and 0.4 mM phosphate. This level of soluble calcium and phosphate corresponds to a $K_{sp}$ of $8.4 \times 10^{-6}$ $M^2$.

In some embodiments, the $K_{sp}$ of the final salt or complex in the fluid media (e.g., 1 in equation (1)) can be different (e.g., greater than) the $K_{sp}$ of the cation-anion salt or complex itself (i.e., no associated impurities, e.g., 2 in equation (2)) in water. For example, referring to equations (1) and (2), the $K_{sp}$ of, e.g., 1 (e.g., MA=calcium phosphate) in the fluid can be different from (e.g., greater than) the $K_{sp}$ of calcium phosphate itself in water (e.g., 2 in equation (2) in which MA=calcium phosphate).

Other implementations of forming the precipitate can be performed. For example, the first cation and the first anion can be introduced into the medium substantially simultaneously or sequentially. In implementations in which the first cation is calcium and the first anion is sulfite, introducing the sulfite into the medium before introducing the calcium into the medium can enhance the precipitation of impurities (Example 2). The concentrations of the first cation and the first anion can be substantially the same or different (cation-rich or anion-rich). For example, the concentration of an ion can be about 1.5 times, about two times, about three times, about four times, or about five times greater than the concentration of the other ion. In some implementations, more than one cation and/or more than one anion are introduced into the medium. The total concentration of the cations can range from about 5 millimolar to about 200 millimolar, as can the total concentration of the anions. Where polymeric solutions are used, the concentration, in mM, may be substantially lower based on the polymer molecular weight; the concentration may instead depend upon the monomer molecular weight. In other implementations, only one or more cation or only one or more anion is introduced into the medium. For example, when the medium containing the protein already includes anion(s) or cation(s) capable of forming a precipitate, then the appropriate cation(s) or anion(s), respectively, can be added to form the precipitate. Alternatively, ions can be added to react with the ions already in the medium to form a first precipitate, and additional cation/anion combination(s) can be added into the medium to form other precipitate(s).

As shown in FIG. 1, the methods can optionally include titrating the medium to an appropriate pH and/or adjusting the temperature (step 34).

In some embodiments, the pH of the medium may be adjusted to a predetermined pH to increase precipitation (step 34). The pH of the medium can be increased or decreased, for example, by titrating with a base (e.g., NaOH) or an acid, such as phosphoric acid or hydrochloric acid. The predetermined pH can be a function of, for example, the cation(s) and anion (s) in the medium, other materials in the medium, and/or the composition of the medium. The predetermined pH can range from about five to about nine, for example, from about 6.5 to about 9.

In other embodiments, the pH of the medium is not adjusted.

In some embodiments, the medium may be heated or chilled to optimize performance (step 34). As with adjusting the pH, the temperature and time for which the medium is heated or incubated can be a function of, for example, the cation(s) and anion(s) in the medium, other materials in the medium, and/or the composition of the medium.

The medium can be incubated at room temperature or heated up, for example, to about 37° C. The incubation or heating period (step 36) can range from about one hour to about twelve hours. While the medium is incubating or heating, the medium can be mixed (e.g., at low speeds to reduce shearing of the materials), or the medium can be mixed for an initial period of time and allowed to sit unmixed so that the precipitate can settle, which allows the protein-containing supernatant to be easily separated.

In other embodiments, the medium is not heated, for example, if precipitation is sufficient to provide good separation.

Next, the medium is centrifuged (step 38) to help separate the precipitate from the supernatant, which reduces the turbidity of the supernatant. Other methods of solids removal are possible, such as depth filtration or microfiltration. As illustrated below in the examples, the turbidity of the medium can be reduced by at least about 30% relative to an untreated control solution in which no flocculation occurred. In some implementations, the turbidity of the medium is reduced by at least by about 50%, at least about 80%, at least about 90%, at least about 95%, or at least about 98% or higher. As used herein, turbidity is measured using a nephalometer (such as those made by HACH, Loveland, Colo.) according to standard procedures.

After primary clarification such as through centrifugation, additional debris removal can occur through the use of filtration (step 38). As illustrated below in the examples, the separation methods described herein can provide high yields, with a protein recovery of at least about 50% (such as at least about 60%, at least about 70%, at least about 80%, or at least about 90%). As used herein, recovery is calculated as the mass of the target protein in the post-treated pool to the mass in the pre-treatment pool. The mass of product is the product of target protein concentration and volume where concentration can be determined by a variety of methods, such as high performance liquid chromatography assays. For target proteins that are antibodies, concentration can often be determined using protein A-based analysis methods. Those skilled in the art of biopharmaceutical cell culture, purification or protein characterization methodologies can identify suitable assay methods.

The protein can be subsequently purified, according to conventional methods.

Proteins or Polypeptides

The present invention relates to the separation of proteins, e.g., soluble or secreted proteins, from a fluid. The term "protein" as used herein refers to one or more polypeptides that can function as a unit. The term "polypeptide" as used herein refers a sequential chain of amino acids linked together via peptide bonds. The term "polypeptide" is used to refer to an amino acid chain of any length, but one of ordinary skill in the art will understand that the term is not limited to lengthy chains and can refer to a minimal chain comprising two amino acids linked together via a peptide bond. If a single polypeptide can function as a unit, the terms "polypeptide" and "protein" may be used interchangeably.

In certain embodiments, the proteins are produced recombinantly. The terms "recombinantly expressed protein" and "recombinant protein" as used herein refer to a polypeptide expressed from a host cell that has been manipulated by the hand of man to express that polypeptide. In certain embodiments, the host cell is a mammalian cell. In certain embodiments, this manipulation may comprise one or more genetic modifications. For example, the host cells may be genetically modified by the introduction of one or more heterologous genes encoding the polypeptide to be expressed. The heterologous recombinantly expressed polypeptide can be identical or similar to polypeptides that are normally expressed in the host cell. The heterologous recombinantly expressed polypeptide can also be foreign to the host cell, e.g., heterologous to polypeptides normally expressed in the host cell. In certain embodiments, the heterologous recombinantly expressed polypeptide is chimeric. For example, portions of a polypeptide may contain amino acid sequences that are identical or similar to polypeptides normally expressed in the host cell, while other portions contain amino acid sequences that are foreign to the host cell. Additionally or alternatively, a polypeptide may contain amino acid sequences from two or more different polypeptides that are both normally expressed in the host cell. Furthermore, a polypeptide may contain amino acid sequences from two or more polypeptides that are both foreign to the host cell. In some embodiments, the host cell is genetically modified by the activation or upregulation of one or more endogenous genes.

Any protein that may desirably be separated in accordance with the present invention will often be selected on the basis of an interesting or useful biological or chemical activity. For example, the present invention may be employed to separate any pharmaceutically or commercially relevant antibody, receptor, cytokine, growth factor, enzyme, clotting factor, hormone, regulatory factor, antigen, binding agent, among others. The following list of proteins that can be separated according to the present invention is merely exemplary in nature, and is not intended to be a limiting recitation. One of ordinary skill in the art will understand that any protein may be expressed in accordance with the present invention and will be able to select the particular protein to be produced based as needed.

Antibodies and Binding Fragments

Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain (VL) and a constant (C) domain (CL). Each heavy chain includes an N-terminal V domain (VH), three or four C domains (CHs), and a hinge region. The CH domain most proximal to VH is designated as CH1. The VH and VL domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is typically the greatest source of molecular diversity within the antibody-binding site. H3, for example, can be as short as two amino acid residues or greater than 26 amino acids. The subunit structures and three-dimensional configurations of different classes of immunoglobulins are well known in the art. For a review of the antibody structure, see *Antibodies: A Laboratory Manual*, Cold Spring Harbor Laboratory, eds. Harlow et al., 1988. One of skill in the art will recognize that each subunit structure, e.g., a CH, VH, CL, VL, CDR, FR structure, comprises active fragments, e.g., the portion of the VH, VL, or CDR subunit the binds to the antigen, i.e., the antigen-binding fragment, or, e.g., the portion of the CH subunit that binds to and/or activates, e.g., an Fc receptor and/or complement. The CDRs typically refer to the Kabat CDRs, as described in *Sequences of Proteins of Immunological Interest*, US Department of Health and Human Services (1991), eds. Kabat et al. Another standard for characterizing the antigen binding site is to refer to the hypervariable loops as described by Chothia. See, e.g., Chothia, D. et al. (1992) *J. Mol. Biol.* 227:799-817; and Tomlinson et al. (1995) *EMBO J.* 14:4628-4638. Still another standard is the AbM definition used by Oxford Molecular's AbM antibody modelling software. See, generally, e.g., *Protein Sequence and Structure Analysis of Antibody Variable Domains*. In: *Antibody Engineering Lab Manual* (Ed.: Duebel, S. and Kontermann, R., Springer-Verlag, Heidelberg). Embodiments described with respect to Kabat CDRs can alternatively be implemented using similar described relationships with respect to Chothia hypervariable loops or to the AbM-defined loops.

As used herein, the term "antibody" includes a protein comprising at least one, and typically two, VH domains or portions thereof, and/or at least one, and typically two, VL domains or portions thereof. In one embodiment, the antibody is a tetramer of two heavy immunoglobulin chains and two light immunoglobulin chains, wherein the heavy and light immunoglobulin chains are inter-connected by, e.g., disulfide bonds. The antibodies, or portions thereof, can be obtained from any origin, including, but not limited to, rodent, primate (e.g., human and non-human primate), camelid (e.g., camel or llama), as well as recombinantly produced, e.g., chimeric, humanized, and/or in vitro generated, as described in more detail herein.

Examples of binding fragments encompassed within the term "antigen-binding fragment" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment, which consists of a VH domain; (vi) a camelid or camelized variable domain; (vii) a single chain Fv (scFv); and (viii) a bispecific antibody. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) *Science* 242:423-26; Huston et al. (1988) *Proc. Natl. Acad. Sci. U.S.A.* 85:5879-83). Such single chain antibodies are also intended to be encompassed within the term "antigen-binding fragment" of an antibody. These fragments are obtained using conventional techniques known to those skilled in the art, and the fragments are evaluated for function in the same manner as are intact antibodies.

The antigen-binding fragment can, optionally, include a moiety that enhances one or more of, e.g., stability, effector cell function or complement fixation. For example, the antigen binding fragment can include a pegylated moiety, albumin, or a heavy and/or a light chain constant region (or a portion thereof).

Other than "bispecific" or "bifunctional" antibodies, an antibody is understood to have each of its binding sites identical. A "bispecific" or "bifunctional antibody," or an antigen-binding fragment thereof, is an artificial hybrid antibody or fragment thereof having two different antigen-binding sites. Bispecific antibodies, or antigen-binding fragments thereof, can be produced by a variety of methods including fusion of hybridomas, linking of Fab' fragments, or recombinantly. See, e.g., Songsivilai & Lachmann, *Clin. Exp. Immunol.* 79:315-321 (1990); Kostelny et al., *J. Immunol.* 148, 1547-1553 (1992).

Numerous methods known to those skilled in the art are available for obtaining antibodies or antigen-binding fragments thereof. For example, monoclonal antibodies may be produced by generation of hybridomas in accordance with known methods. Hybridomas formed in this manner are then screened using standard methods, such as enzyme-linked immunosorbent assay (ELISA) and surface plasmon resonance (Biacore™) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies includes screening protein expression libraries, e.g., phage or ribosome display libraries. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; and WO 90/02809.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized, deimmunized, chimeric, may be produced using recombinant DNA techniques known in the art. A variety of approaches for making chimeric antibodies have been described. See e.g., Morrison et al., *Proc. Natl. Acad. Sci. U.S.A.* 81:6851, 1985; Takeda et al., *Nature* 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

In certain embodiments, a humanized antibody is optimized by the introduction of conservative substitutions, consensus sequence substitutions, germline substitutions and/or backmutations. Such altered immunoglobulin molecules can be made by any of several techniques known in the art, (e.g., Teng et al., Proc. Natl. Acad. Sci. U.S.A., 80: 7308-7312, 1983; Kozbor et al., Immunology Today, 4: 7279, 1983; Olsson et al., Meth. Enzymol., 92: 3-16, 1982), and may be made according to the teachings of PCT Publication WO92/06193 or EP 0239400).

An antibody or fragment thereof may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) J. Mol. Biol. 227:776-798; Cook, G. P. et al. (1995) Immunol. Today Vol. 16 (5): 237-242; Chothia, D. et al. (1992) J. Mol. Biol. 227:799-817; and Tomlinson et al. (1995) EMBO J. 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

In certain embodiments, an antibody can contain an altered immunoglobulin constant or Fc region. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, Annu. Rev. Immunol 9:457-92, 1991; Capel et al., Immunomethods 4:25-34,1994; and de Haas et al., J. Lab. Clin. Med. 126:330-41, 1995).

Non-limiting examples of antibodies that can be separated by the methods of the invention, include but are not limited to, antibodies against Aβ, IL-13, IL-22, GDF8 and 5T4. Each of these antibodies is described in more detail hereinbelow and the appended Examples.

Anti-Aβ Antibodies

As described in the appended Examples, anti-AB antibodies can be separated by the methods of the invention. The terms "AB antibody," "Aβ antibody," "anti-Aβ antibody," and "anti-Aβ" are used interchangeably herein to refer to an antibody that binds to one or more epitopes or antigenic determinants of APP, Aβ protein, or both. Exemplary epitopes or antigenic determinants can be found within the human amyloid precursor protein (APP), but are preferably found within the Aβ peptide of APP. Multiple isoforms of APP exist, for example APP$^{695}$, APP$^{751}$, and APP$^{770}$. Amino acids within APP are assigned numbers according to the sequence of the APP$^{770}$ isoform (see e.g., GenBank Accession No. P05067). Aβ (also referred to herein as beta amyloid peptide and A beta) peptide is a ~4-kDa internal fragment of 39-43 amino acids of APP (Aβ39, Aβ40, Aβ41, Aβ42, and Aβ43). Aβ40, for example, consists of residues 672-711 of APP and Aβ42 consists of residues 672-713 of APP. As a result of proteolytic processing of APP by different secretase enzymes iv vivo or in situ, Aβ is found in both a "short form," 40 amino acids in length, and a "long form," ranging from 42-43 amino acids in length. Epitopes or antigenic determinants can be located within the N-terminus of the Aβ peptide and include residues within amino acids 1-10 of Aβ, preferably from residues 1-3, 1-4, 1-5, 1-6, 1-7, 2-7, 3-6, or 3-7 of Aβ42 or within residues 2-4, 5, 6, 7, or 8 of Aβ, residues 3-5, 6, 7, 8, or 9 of Aβ, or residues 4-7, 8, 9, or 10 of Aβ42. "Central" epitopes or antigenic determinants are located within the central or mid-portion of the Aβ peptide and include residues within amino acids 16-24, 16-23, 16-22, 16-21, 19-21, 19-22, 19-23, or 19-24 of Aβ. "C-terminal" epitopes or antigenic determinants are located within the C-terminus of the Aβ peptide and include residues within amino acids 33-40, 33-41, or 33-42 of Aβ.

In various embodiments, an Aβ antibody is end-specific. As used herein, the term "end-specific" refers to an antibody which specifically binds to the N-terminal or C-terminal residues of an Aβ peptide but that does not recognize the same residues when present in a longer Aβ species comprising the residues or in APP.

In various embodiments, an Aβ antibody is "C-terminus-specific." As used herein, the term "C terminus-specific"

means that the antibody specifically recognizes a free C-terminus of an Aβ peptide. Examples of C terminus-specific Aβ antibodies include those that: recognize an Aβ peptide ending at residue 40, but do not recognize an Aβ peptide ending at residue 41, 42, and/or 43; recognize an Aβ peptide ending at residue 42, but do not recognize an Aβ peptide ending at residue 40, 41, and/or 43; etc.

In one embodiment, the antibody may be a 3D6 antibody or variant thereof, or a 10D5 antibody or variant thereof, both of which are described in U.S. Patent Publication No. 2003/0165496A1, U.S. Patent Publication No. 2004/0087777A1, International Patent Publication No. WO02/46237A3. Description of 3D6 and 10D5 can also be found, for example, in International Patent Publication No. WO02/088306A2 and International Patent Publication No. WO02/088307A2. 3D6 is a monoclonal antibody (mAb) that specifically binds to an N-terminal epitope located in the human β-amyloid peptide, specifically, residues 1-5. By comparison, 10D5 is a mAb that specifically binds to an N-terminal epitope located in the human β-amyloid peptide, specifically, residues 3-6. In another embodiment, the antibody may be a 12B4 antibody or variant thereof, as described in U.S. Patent Publication No. 20040082762A1 and International Patent Publication No. WO03/077858A2. 12B4 is a mAb that specifically binds to an N-terminal epitope located in the human β-amyloid peptide, specifically, residues 3-7. In yet another embodiment, the antibody may be a 12A11 antibody or a variant thereof, as described in U.S. patent application Ser. No. 10/858,855 and International Patent Application No. PCT/US04/17514. 12A11 is a mAb that specifically binds to an N-terminal epitope located in the human β-amyloid peptide, specifically, residues 3-7. In yet another embodiment, the antibody may be a 266 antibody as described in U.S. patent application Ser. No. 10/789,273, and International Patent Application No. WO01/62801A2. Antibodies designed to specifically bind to C-terminal epitopes located in human β-amyloid peptide, for use in the present invention include, but are not limited to, 369.2B, as described in U.S. Pat. No. 5,786,160.

In exemplary embodiments, the antibody is a humanized anti Aβ peptide 3D6 antibody that selectively binds Aβ peptide. More specifically, the humanized anti Aβ peptide 3D6 antibody is designed to specifically bind to an NH$_2$-terminal epitope located in the human β-amyloid 1-40 or 1-42 peptide found in plaque deposits in the brain (e.g., in patients suffering from Alzheimer's disease).

Anti-AB antibodies can be used to treat amyloidogenic diseases, in particular, Alzheimer's Disease. The term "amyloidogenic disease" includes any disease associated with (or caused by) the formation or deposition of insoluble amyloid fibrils. Exemplary amyloidogenic diseases include, but are not limited to, systemic amyloidosis, Alzheimer's disease, mature onset diabetes, Parkinson's disease, Huntington's disease, fronto-temporal dementia, and the prion-related transmissible spongiform encephalopathies (kuru and Creutzfeldt-Jacob disease in humans and scrapie and BSE in sheep and cattle, respectively). Different amyloidogenic diseases are defined or characterized by the nature of the polypeptide component of the fibrils deposited. For example, in subjects or patients having Alzheimer's disease, β-amyloid protein (e.g., wild-type, variant, or truncated β-amyloid protein) is the characterizing polypeptide component of the amyloid deposit. Accordingly, Alzheimer's disease is an example of a "disease characterized by deposits of Aβ" or a "disease associated with deposits of Aβ," e.g., in the brain of a subject or patient. The terms "β-amyloid protein," "β-amyloid peptide," "β-amyloid," "Aβ," and "Aβ peptide" are used interchangeably herein.

Anti-5T4 Antibodies

The 5T4 antigen has been previously characterized (see e.g., WO 89/07947). The full nucleic acid sequence of human 5T4 is known (Myers et al. (1994) *J Biol Chem* 169: 9319-24 and GenBank at Accession No. Z29083). The sequence for 5T4 antigen from other species is also known, for example, murine 5T4 (WO00/29428), canine 5T4 (WO01/36486) or feline 5T4 (US 05/0100958).

Human 5T4 is a glycoprotein of about 72 kDa expressed widely in carcinomas, but having a highly restricted expression pattern in normal adult tissues. It appears to be strongly correlated to metastasis in colorectal and gastric cancer. Expression of the 5T4 antigen is also found at high frequency in breast and ovarian cancers (Starzynska et al. (1998) *Eur. J. Gastroenterol. Hepatol.* 10:479-84; Starzynska et al. (1994) *Br. J. Cancer* 69:899-902; Starzynska et al. (1992) *Br. J. Cancer* 66:867-9). 5T4 has been proposed as a marker, with possible mechanistic involvement, for tumor progression and metastasis potential (Carsberg et al. (1996) *Int J Cancer* 68:84-92). 5T4 has also been proposed for use as an immunotherapeutic agent (see WO 00/29428). Antigenic peptides of 5T4 are disclosed in, e.g., US 05/0100958, the contents of which are incorporated by reference.

Several pending applications relate generally to nucleic acids encoding the anti-5T4 monoclonal antibody, vectors and host cells thereof, for example, U.S. Application Publication Nos. 2003/0018004 and 2005/0032216. A provisional patent application pertaining generally to the humanized anti-5T4 H8 monoclonal antibodies and calicheamicin conjugates thereof, as well as methods of treatment using these calicheamicin conjugates has been filed (U.S. Application Publication No. 2006/0088522). The contents of all of these applications are incorporated by reference herein in their entirety.

Anti-IL13 Antibodies

Another exemplary antibodies that can be separated by the methods of the invention are anti-IL-13 antibodies. Interleukin-13 (IL-13) is a previously characterized cytokine secreted by T lymphocytes and mast cells (McKenzie et al. (1993) *Proc. Natl. Acad. Sci. USA* 90:3735-39; Bost et al. (1996) *Immunology* 87:663-41). The term "IL-13" refers to interleukin-13, including full-length unprocessed precursor form of IL-13, as well as the mature forms resulting from post-translational cleavage. The term also refers to any fragments and variants of IL-13 that maintain at least some biological activities associated with mature IL-13, including sequences that have been modified (e.g., recombinantly modified). The term "IL-13" includes human IL-13, as well as other vertebrate species. Several pending applications disclose antibodies against human and monkey IL-13, IL-13 peptides, vectors and host cells producing the same, for example, U.S. Application Publication Nos. 2006/0063228A and 2006/0073148. The contents of all of these publications are incorporated by reference herein in their entirety.

IL-13 shares several biological activities with IL-4. For example, either IL-4 or IL-13 can cause IgE isotype switching in B cells (Tomkinson et al. (2001) *J. Immunol.* 166:5792-5800). Additionally, increased levels of cell surface CD23 and serum CD23 (sCD23) have been reported in asthmatic patients (Sanchez-Guererro et al. (1994) *Allergy* 49:587-92; DiLorenzo et al. (1999) *Allergy Asthma Proc.* 20:119-25). In addition, either IL-4 or IL-13 can upregulate the expression of MHC class II and the low-affinity IgE receptor (CD23) on B cells and monocytes, which results in enhanced antigen presentation and regulated macrophage function (Tomkinson et al., supra). These observations suggest that IL-13 may be an important player in the development of airway eosinophilia and airway hyperresponsiveness (AHR) (Tomkinson et al., supra; Wills-Karp et al. (1998) *Science* 282:2258-61). Accordingly, inhibition of IL-13 can be useful in ameliorating the pathology of a number of inflammatory and/or allergic conditions, including, but not limited to, respiratory disorders, e.g., asthma; chronic obstructive pulmonary disease (COPD); other conditions involving airway inflammation, eosinophilia, fibrosis and excess mucus production, e.g., cystic fibrosis and pulmonary fibrosis; atopic disorders, e.g., atopic dermatitis, urticaria, eczema, allergic rhinitis; inflammatory and/or autoimmune conditions of, the skin (e.g., atopic dermatitis), gastrointestinal organs (e.g., inflammatory bowel diseases (IBD), such as ulcerative colitis and/or Crohn's disease), liver (e.g., cirrhosis, hepatocellular carcinoma); scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus).

Anti-IL22 Antibodies

Another exemplary antibodies that can be separated by the methods of the invention are anti-IL-22 antibodies. Interleukin-22 (IL-22) is a previously characterized class II cytokine that shows sequence homology to IL-10. Its expression is up-regulated in T cells by IL-9 or ConA (Dumoutier L. et al. (2000) *Proc Natl Acad Sci USA* 97(18):10144-9). Studies have shown that expression of IL-22 mRNA is induced in vivo in response to LPS administration, and that IL-22 modulates parameters indicative of an acute phase response (Dumoutier L. et al. (2000) supra; Pittman D. et al. (2001) *Genes and Immunity* 2:172), and that a reduction of IL-22 activity by using a neutralizing anti-IL-22 antibody ameliorates inflammatory symptoms in a mouse collagen-induced arthritis (CIA) model. Thus, IL-22 antagonists, e.g., neutralizing anti-IL-22 antibodies and fragments thereof, can be used to induce immune suppression in vivo, for examples, for treating autoimmune disorders (e.g., arthritic disorders such as rheumatoid arthritis); respiratory disorders (e.g., asthma, chronic obstructive pulmonary disease (COPD)); inflammatory conditions of, e.g., the skin (e.g., psoriasis), cardiovascular system (e.g., atherosclerosis), nervous system (e.g., Alzheimer's disease), kidneys (e. g., nephritis), liver (e.g., hepatitis) and pancreas (e.g., pancreatitis).

The term "IL-22" refers to interleukin-22, including full-length unprocessed precursor form of IL-22, as well as the mature forms resulting from post-translational cleavage. The term also refers to any fragments and variants of IL-22 that maintain at least some biological activities associated with mature IL-22, including sequences that have been modified. The term "IL-22" includes human IL-22, as well as other vertebrate species. The amino acid and nucleotide sequences of human and rodent IL-22, as well as antibodies against IL-22 are disclosed in, for example, U.S. Application Publication Nos. 2005-0042220 and 2005-0158760, and U.S. Pat. No. 6,939,545. The contents of all of these publications are incorporated by reference herein in their entirety.

Anti-GDF8 Antibodies

Yet another exemplary antibodies that can be separated by the methods of the invention are anti-GDF8 antibodies. Growth and differentiation factor-8 (GDF-8), also known as myostatin, is a secreted protein and is a member of the transforming growth factor-beta (TGF-β) superfamily of structurally related growth factors, all of which possess physiologically important growth-regulatory and morphogenetic properties (Kingsley et al. (1994) *Genes Dev.*, 8: 133-146; Hoodless et al. (1998) *Curr. Topics Microbiol. Immunol.*, 228: 235-272). Similarly to TGF-β, human GDF-8 is synthesized as a 375 amino acid long precursor protein. The precursor GDF-8 protein forms a homodimer. During processing the amino-terminal propeptide is cleaved off at Arg-266. The cleaved propeptide, known as the "latency-associated peptide" (LAP), may remain noncovalently bound to the homodimer, thereby inactivating the complex (Miyazono et al. (1988) *J. Biol. Chem.* 263: 6407-6415; Wakefield et al. (1988) *J. Biol. Chem.* 263: 7646-7654; Brown et al. (1990) *Growth Factors*, 3: 35-43; and Thies et al. (2001) *Growth Factors*, 18: 251-259). The complex of mature GDF-8 with propeptide is commonly referred to as the "small latent complex" (Gentry et al. (1990) *Biochemistry*, 29: 6851-6857; Derynck et al. (1995) *Nature*, 316: 701-705; and Massague (1990) *Ann. Rev. Cell Biol.*, 12: 597-641). Other proteins are also known to bind to mature GDF-8 and inhibit its biological activity. Such inhibitory proteins include follistatin and follistatin-related proteins (Gamer et al. (1999) *Dev. Biol.*, 208: 222-232).

The term "GDF-8" refers to growth and differentiation factor-8 and, where appropriate, factors that are structurally or functionally related to GDF-8, for example, BMP-11 and other factors belonging to the TGF-β superfamily. The term refers to the full-length unprocessed precursor form of GDF-8, as well as the mature and propeptide forms resulting from post-translational cleavage. The term also refers to any fragments and variants of GDF-8 that maintain at least some biological activities associated with mature GDF-8, including sequences that have been modified. The amino acid sequence human GDF-8, as well as many other vertebrate species (including murine, baboon, bovine, chicken) is disclosed, e.g., US 2004-0142382, US 2002-0157125, and McPherron et al. (1997) *Proc. Nat. Acad. Sci.* U.S.A., 94:12457-12461; the contents of all of which are hereby incorporated by reference in their entirety). Examples of neutralizing antibodies against GDF-8 are disclosed in, e.g., US 2004-0142382, and may be used to treat or prevent conditions in which an increase in muscle tissue or bone density is desirable. Exemplary disease and disorders include muscle and neuromuscular disorders such as muscular dystrophy (including Duchenne's muscular dystrophy); amyotrophic lateral sclerosis; muscle atrophy; organ atrophy; frailty; tunnel syndrome; congestive obstructive pulmonary disease; sarcopenia, cachexia, and other muscle wasting syndromes; adipose tissue disorders (e.g., obesity); type 2 diabetes; impaired glucose tolerance; metabolic syndromes (e.g., syndrome X); insulin resistance induced by trauma such as burns or nitrogen imbalance; and bone degenerative diseases (e.g., osteoarthritis and osteoporosis)

Soluble Receptors and Receptor Fusions

In some embodiments, proteins separated by the methods of the invention can be soluble receptors or fragments thereof. Examples of soluble receptors include the extracellular domain of a receptor, such as soluble tumor necrosis factor alpha and beta receptors (TNFR-1; EP 417,563 published Mar. 20, 1991; TNFR-2, EP 417,014 published Mar. 20, 1991; and reviewed in Naismith and Sprang, *J Inflamm.* 47(1-2):1-7, 1995-96, each of which is incorporated herein by reference in its entirety). In other embodiments, the soluble receptor includes the extracellular domain of interleukin-21 receptor (IL-21R) as described in, for example, US 2003-0108549 (the contents of which are also incorporated by reference).

In other embodiments, the methods of the invention are used to separate soluble receptor fusions. The fusion protein can include a targeting moiety, e.g., a soluble receptor fragment or a ligand, and an immunoglobulin chain, an Fc fragment, a heavy chain constant regions of the various isotypes, including: IgG1, IgG2, IgG3, IgG4, IgM, IgA1, IgA2, IgD, and IgE. For example, the fusion protein can include the extracellular domain of a receptor, and, e.g., fused to, a human immunoglobulin Fc chain (e.g., human IgG, e.g., human IgG1 or human IgG4, or a mutated form thereof). In one embodiment, the human Fc sequence has been mutated at one or more amino acids, e.g., mutated at residues 254 and 257 from the wild type sequence to reduce Fc receptor binding. The fusion proteins may additionally include a linker sequence joining the first moiety to the second moiety, e.g., the immunoglobulin fragment. For example, the fusion protein can include a peptide linker, e.g., a peptide linker of about 4 to 20, more preferably, 5 to 10, amino acids in length; the peptide linker is 8 amino acids in length. For example, the fusion protein can include a peptide linker having the formula (Ser-Gly-Gly-Gly-Gly)y wherein y is 1, 2, 3, 4, 5, 6, 7, or 8. In other embodiments, additional amino acid sequences can be added to the N- or C-terminus of the fusion protein to facilitate expression, steric flexibility, detection and/or isolation or purification.

In certain embodiments, the soluble receptor fusion comprises a soluble TNFR-Ig (e.g., a soluble fragment of a TNF receptor, e.g., p55 or p75 human TNF receptor or derivatives thereof, e.g., 75 kd TNFR-IgG (e.g., 75 kD TNF receptor fused to an Fc portion of human IgG1).

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *Current Protocols in Molecular Biology*, John Wiley & Sons, 1992). Moreover, many expression vectors are commercially available that encode a fusion moiety (e.g., an Fc region of an immunoglobulin heavy chain). Immunoglobulin fusion polypeptide are known in the art and are described in e.g., U.S. Pat. Nos. 5,516,964; 5,225,538; 5,428,130; 5,514,582; 5,714,147; and 5,455,165.

Growth Factors and Cytokines

Another class of polypeptides that have been shown to be effective as pharmaceutical and/or commercial agents and that can desirably be produced according to the teachings of the present invention includes growth factors and other signaling molecules, such as cytokines.

Growth factors are typically glycoproteins that are secreted by cells and bind to and activate receptors on other cells, initiating a metabolic or developmental change in the receptor cell. Non-limiting examples of mammalian growth factors and other signaling molecules include cytokines; epidermal growth factor (EGF); platelet-derived growth factor (PDGF); fibroblast growth factors (FGFs) such as aFGF and bFGF; transforming growth factors (TGFs) such as TGF-alpha and TGF-beta, including TGF-beta 1, TGF-beta 2, TGF-beta 3, TGF-beta 4, or TGF-beta 5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-13 (e.g., IL-11); tumor necrosis factor (TNF) alpha and beta; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin, hemopoietic growth factor; enkephalinase; RANTES (regulated on activation normally T-cell expressed and secreted); human macrophage inflammatory protein (MIP-1-alpha); mullerian-inhibiting substance; relaxin A-chain; relaxin B-chain; pro-relaxin; mouse gonadotropin-associated peptide; neurotrophic factors such as bone-derived neurotrophic factor (BDNF), neurotrophin-3, -4, -5, or -6 (NT-3, NT-4, NT-5, or NT-6), or a nerve growth factor such as NGF-beta. One of ordinary skill in the art will be aware of other growth factors or signaling molecules that can be expressed in accordance with methods and compositions of the present invention.

Specific alterations in the glycosylation pattern of growth factors or other signaling molecules have been shown to have dramatic effects on their therapeutic properties. As one example, a common method of treatment for patients who suffer from chronic anemia is to provide them with frequent injections of recombinant human erythropopietin (rHuEPO) in order to boost their production of red blood cells. An analog of rHuEPO, darbepoetin alfa (Aranesp®), has been developed to have a longer duration than normal rHuEPO. The primary difference between darbepoetin alfa and rHuEPO is the presence of two extra sialic-acid-containing N-linked oligosaccharide chains. Production of darbepoetin alfa has been accomplished using in vitro glycoengineering (see Elliott et al., *Nature Biotechnology* 21(4):414-21, 2003, incorporated herein by reference in its entirety). Elliott et al. used in vitro mutagenesis to incorporate extra glycosylation sites into the rHuEPO polypeptide backbone, resulting in expression of the darbepoetin alfa analog. The extra oligosaccharide chains are located distal to the EPO receptor binding site and apparently do not interfere with receptor binding. However, darbepoetin alfa's half-life is up to three-fold higher than rHuEPO, resulting in a much more effective therapeutic agent.

Clotting Factors

Clotting factors have been shown to be effective as pharmaceutical and/or commercial agents. Hemophilia B is a disorder in which the blood of the sufferer is unable to clot. Thus, any small wound that results in bleeding is potentially a life-threatening event. For example, Coagulation Factor IX (Factor IX or "FIX") is a single-chain glycoprotein whose deficiency results in Hemophilia B. FIX is synthesized as a single chain zymogen that can be activated to a two-chain serine protease (Factor IXa) by release of an activation peptide. The catalytic domain of Factor IXa is located in the heavy chain (see Chang et al., *J. Clin. Invest.*, 100:4, 1997, incorporated herein by reference in its entirety). FIX has multiple glycosylation sites including both N-linked and 0-linked carbohydrates. One particular O-linked structure at Serine 61 (Sia-α2,3-Gal-α1,4-GlcNAc-β1,3-Fuc-α1-O-Ser) was once thought unique to FIX but has since found on a few other molecules including the Notch protein in mammals and

*Drosophila* (Maloney et al, *Journal of Biol. Chem.*, 275(13), 2000). FIX produced by Chinese Hamster Ovary ("CHO") cells in cell culture exhibits some variability in the Serine 61 oligosaccharide chain. These different glycoforms, and other potential glycoforms, may have different abilities to induce clotting when administered to humans or animals and/or may have different stabilities in the blood, resulting in less effective clotting.

Hemophilia A, which is clinically indistinguishable from Hemophilia B, is caused by a defect in human clotting factor VIII, another glycoprotein that is synthesized as a single chain and then processed into a two-chain active form. The present invention may also be employed to control or alter the glycosylation pattern of clotting factor VIII in order to modulate its clotting activity. Other clotting factors that can be produced in accordance with the present invention include tissue factor and von Willebrands factor.

Enzymes

Another class of polypeptides that have been shown to be effective as pharmaceutical and/or commercial agents and that can desirably be produced according to the teachings of the present invention includes enzymes. Enzymes may be glycoproteins whose glycosylation pattern affects enzymatic activity. Thus, the present invention may also be used to produce enzymes in a cell culture wherein the produced enzymes have a more extensive or otherwise more desirable glycosylation pattern.

As but one non-limiting example, a deficiency in glucocerebrosidase (GCR) results in a condition known as Gaucher's disease, which is caused by an accumulation of glucocerebrosidase in lysosomes of certain cells. Subjects with Gaucher's disease exhibit a range of symptoms including splenomegaly, hepatomegaly, skeletal disorder, thrombocytopenia and anemia. Friedman and Hayes showed that recombinant GCR (rGCR) containing a single substitution in the primary amino acid sequence exhibited an altered glycosylation pattern, specifically an increase in fucose and N-acetyl glucosamine residues compared to naturally occurring GCR (see U.S. Pat. No. 5,549,892).

Friedman and Hayes also demonstrated that this rGCR exhibited improved pharmacokinetic properties compared to naturally occurring rGCR. For example, approximately twice as much rGCR targeted liver Kupffer cells than did naturally occurring GCR. Although the primary amino acid sequences of the two proteins differed at a single residue, Friedman and Hayes hypothesized that the altered glycosylation pattern of rGCR may also influence the targeting to Kupffer cells. One of ordinary skill in the art will be aware of other known examples of enzymes that exhibit altered enzymatic, pharmacokinetic and/or pharmacodynamic properties resulting from an alteration in their glycosylation patterns.

Protein Production

Proteins separated by the methods of the invention can be produced recombinantly using techniques well known in the art. Nucleotide sequence encoding the proteins are typically inserted in an expression vector for introduction into host cells that may be used to produce the desired quantity of modified antibody that, in turn, provides the polypeptides. The term "vector" includes a nucleic acid construct often including a nucleic acid, e.g., a gene, and further including minimal elements necessary for nucleic acid replication, transcription, stability and/or protein expression or secretion from a host cell. Such constructs may exist as extrachromosomal elements or may be integrated into the genome of a host cell.

The term "expression vector" includes a specific type of vector wherein the nucleic acid construct is optimized for the high-level expression of a desired protein product. Expression vectors often have transcriptional regulatory agents, such as promoter and enhancer elements, optimized for high-levels of transcription in specific cell types and/or optimized such that expression is constitutive based upon the use of a specific inducing agent. Expression vectors further have sequences that provide for proper and/or enhanced translation of the protein As known to those skilled in the art, such vectors may easily be selected from the group consisting of plasmids, phages, viruses, and retroviruses. The term "expression cassette" includes a nucleic acid construct containing a gene and having elements in addition to the gene that allow for proper and or enhanced expression of that gene in a host cell. For producing antibodies, nucleic acids encoding light and heavy chains can be inserted into expression vectors. Such sequences can be present in the same nucleic acid molecule (e.g., the same expression vector) or alternatively, can be expressed from separate nucleic acid molecules (e.g., separate expression vectors).

The term "operably linked" includes a juxtaposition wherein the components are in a relationship permitting them to function in their intended manner (e.g., functionally linked). As an example, a promoter/enhancer operably linked to a polynucleotide of interest is ligated to said polynucleotide such that expression of the polynucleotide of interest is achieved under conditions which activate expression directed by the promoter/enhancer.

Expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences (see, e.g., Itakura et al., U.S. Pat. No. 4,704,362). In addition to the immunoglobulin DNA cassette sequences, insert sequences, and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin, or methotrexate, on a host cell into which the vector has been introduced. Preferred selectable marker genes include the dihydrofolate reductase (DHFR) gene (for use in dhfr host cells with methotrexate selection/amplification) and the neo gene (for G418 selection).

Once the vector has been incorporated into the appropriate host cell, the host cell is maintained under conditions suitable for high level expression of the nucleotide sequences, and the collection and purification of the desired antibodies. Any host cell susceptible to cell culture, and to expression of proteins or polypeptides, may be utilized in accordance with the present invention. In certain embodiments, the host cell is mammalian. Non-limiting examples of mammalian cells that may be used in accordance with the present invention include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59, 1977); baby hamster kidney cells (BHK, ATCC CCL 10); Chinese hamster ovary cells+/−DHFR (CHO, Urlaub and Chasin, *Proc. Natl. Acad. Sci.* USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Expression vectors for these cells can include expression control sequences, such as an origin of replication, a promoter, and an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from immunoglobulin genes, SV40, adenovirus, bovine papilloma virus, cytomegalovirus and the like. See, e.g., Co et al., (1992) *J. Immunol.* 148:1149. Preferred regulatory sequences for mammalian host cell expression include viral elements that direct high levels of protein expression in mammalian cells, such as promoters and/or enhancers derived from FF-1a promoter and BGH polyA, cytomegalovirus (CMV) (such as the CMV promoter/enhancer), Simian Virus 40 (SV40) (such as the SV40 promoter/enhancer), adenovirus (e.g., the adenovirus major late promoter (AdMLP)), and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffer et al. In exemplary embodiments, the antibody heavy and light chain genes are operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. In exemplary embodiments of the invention, the construct include an internal ribosome entry site (IRES) to provide relatively high levels of polypeptides of the invention in eukaryotic host cells. Compatible IRES sequences are disclosed in U.S. Pat. No. 6,193, 980 that is also incorporated herein.

Alternatively, coding sequences can be incorporated in a transgene for introduction into the genome of a transgenic animal and subsequent expression in the milk of the transgenic animal (see, e.g., Deboer et al., U.S. Pat. No. 5,741,957, Rosen, U.S. Pat. No. 5,304,489, and Meade et al., U.S. Pat. No. 5,849,992). Suitable transgenes include coding sequences for light and/or heavy chains in operable linkage with a promoter and enhancer from a mammary gland specific gene, such as casein or beta lactoglobulin.

Prokaryotic host cells may also be suitable for producing the antibodies of the invention. *E. coli* is one prokaryotic host particularly useful for cloning the polynucleotides (e.g., DNA sequences) of the present invention. Other microbial hosts suitable for use include bacilli, such as *Bacillus subtilis*, enterobacteriaceae, such as *Escherichia, Salmonella*, and *Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Expression of proteins in prokaryotes is most often carried out in *E. coli* with vectors containing constitutive or inducible promoters directing the expression of either fusion or non-fusion proteins. Fusion vectors add a number of amino acids to an antibody encoded therein, often to the constant region of the recombinant antibody, without affecting specificity or antigen recognition of the antibody. Addition of the amino acids of the fusion peptide can add additional function to the antibody, for example as a marker (e.g., epitope tag such as myc or flag).

Other microbes, such as yeast, are also useful for expression. *Saccharomyces* is a preferred yeast host, with suitable vectors having expression control sequences (e.g., promoters), an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

The vectors containing the polynucleotide sequences of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment, electroporation, lipofection, biolistics or viral-based transfection may be used for other cellular hosts. (See generally Sambrook et al., *Molecular Cloning: A Laboratory Manual* (Cold Spring Harbor Press, 2nd ed., 1989), incorporated by reference herein in its entirety for all purposes.). Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

When heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms of the present invention can be separated as described herein and/or further purified according to procedures known in the art, including ammonium sulfate precipitation, affinity columns, column chromatography, HPLC purification, gel electrophoresis and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

The following examples are illustrative and not intended to be limiting.

Example 1

Flocculation with various cations and anions: Various monoclonal antibodies (mAb) (shown in Table 1) were produced by recombinant Chinese Hamster Ovary (CHO) cells cultured in serum free media. Approximately 50 mL of the cell-containing conditioned media was aliquoted in to 125 mL Erlenmeyer flasks (except the 30/20 calcium phosphate example with anti-GDF8 #2 which had 400 mL in a 1000 mL flask and the 30/20 calcium phosphate example with anti-IL13 #1 which had 1000 mL in a 200 mL flask). HEPES was added to 40 mM to control the pH. A concentrated solution of metal cations was added to the solution to achieve a final target concentration (see Table 1) and mixed gently. A concentrated solution of anions was added to the mixture (see Table 1) to achieve the final anion concentration and mixed gently (in some of the examples, indicated by an asterisk (*) in Table 1 below, the anion was added first and the cation second). The pH was increased by the addition of NaOH or decreased by the addition of HCl to the targeted pH range. In many of the examples, the pH did not need to be adjusted. The mixture was allowed to incubate on a shaker at 18-25° C. for one to four hours along with negative controls. After the incubation, the mixture was poured into a 50 mL centrifuge tube. Each mixture was spun at 340 g for ten minutes. The clarified supernatant was aliquoted and the turbidity measured using a nephalometer (HACH, Loveland Colo.). The resulting turbidity is reported in Table 1 as a percent reduction from that of the untreated control. The antibody concentration was measured by a Protein A HPLC method general to antibodies. The recovery as compared to the untreated control is reported in Table 1.

TABLE 1

Flocculation results for the cations calcium, magnesium, manganese, cobalt (II), and nickel. . All treatments were performed with the addition of cation prior to anion, except where noted by an asterisk (*), where the anion was added prior to the cation.

| Anion | Cation/Anion (mM) | Product of Concentrations ($M^2$) | pH | mAb | % Turbidity Reduction | % Product Recovery |
|---|---|---|---|---|---|---|
| Calcium ||||||| 
| Phosphate | 20/20 | 4.0E−04 | 6.5 | anti-AB #1 | 65% | 91% |
| Phosphate | 40/40 | 1.6E−03 | 6.0 | anti-AB #1 | 89% | 77% |
| Phosphate | 80/80 | 6.4E−03 | 5.4 | anti-AB #1 | 95% | 56% |
| Phosphate | 40/40 | 1.6E−03 | 7 | anti-AB #1 | 73% | 90% |
| Phosphate | 40/40 | 1.6E−03 | 7.5 | anti-AB #1 | 74% | 87% |
| Phosphate | 20/20 | 4.0E−04 | 6.5 | anti-AB #1 | 82% | 92% |
| Phosphate | 20/20 | 4.0E−04 | 6.0 | anti-AB #1 | 53% | 95% |
| Phosphate | 40/40 | 1.6E−03 | 6.5 | anti-AB #1 | 96% | 79% |
| Phosphate | 40/40 | 1.6E−03 | 6.0 | anti-AB #1 | 96% | 80% |
| Phosphate | 10/10 | 1.0E−04 | 7 | anti-AB #1 | 42% | 112% |
| Phosphate | 20/20 | 4.0E−04 | 6.5 | anti-AB #1 | 81% | 93% |
| Phosphate | 20/20 | 4.0E−04 | 7.0 | anti-AB #1 | 81% | 94% |
| Phosphate | 20/20 | 4.0E−04 | 7.5 | anti-AB #1 | 86% | 97% |
| Phosphate | 20/40 | 8.0E−04 | 6.5 | anti-AB #1 | 68% | 92% |
| Phosphate | 20/40 | 8.0E−04 | 7.0 | anti-AB #1 | 67% | 92% |
| Phosphate | 20/40 | 8.0E−04 | 7.5 | anti-AB #1 | 61% | 107% |
| Phosphate | 40/20 | 8.0E−04 | 6.5 | anti-AB #1 | 98% | 82% |
| Phosphate | 40/20 | 8.0E−04 | 7.0 | anti-AB #1 | 98% | 96% |
| Phosphate | 40/20 | 8.0E−04 | 7.5 | anti-AB #1 | 98% | 97% |
| Phosphate | 40/40 | 1.6E−03 | 6.5 | anti-AB #1 | 92% | 83% |
| Phosphate | 40/40 | 1.6E−03 | 7.0 | anti-AB #1 | 89% | 88% |
| Phosphate | 40/40 | 1.6E−03 | 7.5 | anti-AB #1 | 88% | 91% |
| Phosphate | 20/13.3 | 2.7E−04 | 7.3 | anti-AB #1 | 68% | 84% |
| Phosphate | 50/33.3 | 1.7E−03 | 6.5-6.8 | anti-AB #1 | 96% | 64% |
| Phosphate | 20/13.3 | 2.7E−04 | 7.3 | anti-GDF8 #1 | 90% | 91% |
| Phosphate | 20/13.3 | 2.7E−04 | 8.9 | anti-GDF8 #1 | 68% | 80% |
| Sulfite* | 50/33.3 | 1.7E−03 | 7.5 | anti-GDF8 #1 | 46% | 94% |
| Phosphate* | 30/20 | 6.0E−04 | 7.3 | anti-AB #1 | 96% | 96% |
| Phosphate* | 20/13.3 | 2.7E−04 | 7.2 | anti-AB #1 | 78% | 94% |
| Sulfite* | 50/50 | 2.5E−03 | 7.6 | anti-AB #1 | 56% | 91% |
| Carbonate* | 50/50 | 2.5E−03 | 8.7 | anti-AB #1 | 79% | 95% |
| Fluoride* | 50/10 | 5.0E−04 | 7.5 | anti-AB #1 | 93% | 84% |
| Silicate* | 50/50 | 2.5E−03 | 9.2 | anti-GDF8 #1 | 88% | 90% |
| Molybdate* | 50/50 | 2.5E−03 | 8.0 | anti-GDF8 #1 | 30% | 95% |
| Phosphate* | 30/20 | 6.0E−04 | 7.0-7.5 | anti-AB #1 | 83% | 91% |
| Phosphate* | 30/20 | 6.0E−04 | 7.0-7.5 | anti-AB #2 | 93% | 100% |
| Phosphate* | 30/20 | 6.0E−04 | 7.0-7.5 | anti-GDF8 #1 | 80% | 99% |
| Phosphate* | 30/20 | 6.0E−04 | 7.0-7.5 | anti-IL13 #2 | 93% | 94% |
| Phosphate* | 30/20 | 6.0E−04 | 7.0-7.5 | anti-IL13 #2 | 92% | 93% |
| Phosphate* | 30/20 | 6.0E−04 | 7.0-7.5 | anti-IL13 #2 | 94% | 97% |
| Phosphate* | 30/20 | 6.0E−04 | 7.0-7.5 | anti-IL13 #2 | 89% | 96% |
| Phosphate* | 30/20 | 6.0E−04 | 7.0-7.5 | anti-IL13 #2 | 93% | 94% |
| Phosphate* | 30/20 | 6.0E−04 | 7.0-7.5 | anti-IL13 #2 | 95% | 96% |
| Phosphate* | 30/20 | 6.0E−04 | 7.0-7.5 | anti-IL22 | 97% | 100% |
| Phosphate* | 24/16 | 3.8E−04 | 7.0-7.5 | anti-AB #1 | 84% | 93% |
| Phosphate* | 24/16 | 3.8E−04 | 7.0-7.5 | anti-IL22 | 95% | 102% |
| Phosphate* | 24/16 | 3.8E−04 | 7.0-7.5 | anti-AB #1 | 83% | 95% |

TABLE 1-continued

Flocculation results for the cations calcium, magnesium, manganese, cobalt (II), and nickel. . All treatments were performed with the addition of cation prior to anion, except where noted by an asterisk (*), where the anion was added prior to the cation.

| Anion | Cation/Anion (mM) | Product of Concentrations (M$^2$) | pH | mAb | % Turbidity Reduction | % Product Recovery |
|---|---|---|---|---|---|---|
| Phosphate* | 24/16 | 3.8E−04 | 7.0-7.5 | anti-IL13 #1 | 93% | 94% |
| Phosphate* | 40/20 | 8.0E−04 | 7.0-7.5 | anti-IL13 #2 | 96% | 85% |
| Phosphate* | 80/20 | 1.6E−03 | 6.5-6.7 | anti-AB #1 | 98% | 62% |
| Phosphate* | 30/20 | 6.0E−04 | 7.0-7.5 | anti-GDF8 #2 | 92% | 97% |
| Phosphate* | 30/20 | 6.0E−04 | 7.0-7.5 | anti-IL13 #1 | 98% | 97% |
| Magnesium | | | | | | |
| Carbonate | 200/133 | 2.7E−02 | 9 | anti-AB #1 | 70% | 100% |
| Phosphate | 200/133 | 2.7E−02 | 8 | anti-GDF8 #1 | 77% | 95% |
| Phosphate | 200/133 | 2.7E−02 | 9 | anti-GDF8 #1 | 77% | 90% |
| Fluoride* | 50/10 | 5.0E−04 | 7.4 | anti-AB #1 | 97% | 89% |
| Phosphate* | 50/33.3 | 1.7E−03 | 8 | anti-AB #1 | 54% | 91% |
| Phosphate* | 100/66.7 | 6.7E−03 | 8 | anti-AB #1 | 43% | 88% |
| Manganese (II) | | | | | | |
| Phosphate | 20/13.3 | 2.7E−04 | 6.9 | anti-AB #1 | 79% | 99% |
| Carbonate | 20/13.3 | 2.7E−04 | 7.4 | anti-AB #1 | 59% | 96% |
| Phosphate | 20/13.3 | 2.7E−04 | 7.2 | anti-GDF8 #1 | 81% | 85% |
| Cobalt (II) | | | | | | |
| Phosphate* | 30/20 | 6.0E−04 | 7.1 | anti-AB #1 | 78% | 74% |
| Nickel | | | | | | |
| Phosphate | 20/13.3 | 2.7E−04 | 8 | anti-GDF8 #1 | 58% | 63% |
| Carbonate | 20/13.3 | 2.7E−04 | 8 | anti-GDF8 #1 | 42% | 62% |

The residual levels of calcium and phosphate in the supernatants of some samples were measured. Calcium residuals were measured using a BioAssay Systems QuantiChrom Calcium Assay Kit (DICA-500). Phosphate residuals were measured using a BioAssay Systems Malachite Green Phosphate Assay Kit (POMG-25H). In the anti-IL13 #2 sample with 40 mM calcium and 20 mM phosphate in Table 1, the supernatant after centrifugation contained 8.19 mM calcium and 1.04 mM phosphate. This level of soluble calcium and phosphate translates to a $K_{sp}$ of $8.5 \times 10^{-6}$ M$^2$. In the anti-AB #1 sample with 80 mM calcium and 20 mM phosphate in Table 1, the supernatant after centrifugation contained 22.2 mM calcium and 0.4 mM phosphate. This level of soluble calcium and phosphate translates to a $K_{sp}$ of $8.4 \times 10^{-6}$ M$^2$.

Example 2

Effect of order of anion/cation addition: A mAb, anti-GDF8 #1 was produced by recombinant CHO cells cultured in serum free media. Approximately 50 mL of the cell-containing conditioned media was aliquoted into 3×125 mL Erlenmeyer flasks, A, B, and C. Sample A was left untreated and served as a negative control. HEPES was added to 40 mM to control the pH in Samples B and C. 5M calcium chloride was added to Sample B to a concentration of 50 mM; after gentle mixing, 0.5M sodium sulfite was added to a concentration of 33.3 mM. For Sample C, the order of addition was reversed. 0.5M sodium sulfite was added to a concentration of 33.3 mM; after gentle mixing, 5M calcium chloride was added to a concentration of 50 mM. All three mixtures had pHs between 7.4 and 7.6. The mixtures were allowed to incubate on a shaker for one hour at 18-25° C. After the incubation, the mixtures were poured into 50 mL centrifuge tubes. Each mixture was spun at 340 g for ten minutes. The clarified supernatant was removed and assayed for antibody concentration by Protein A HPLC, and for turbidity using a nephalometer.

Samples B and C both had antibody recoveries of 94% as compared to the untreated sample. Sample B, with the cation added first, showed an increase in turbidity as compared to the untreated sample, indicating a precipitate had formed, but that it was too small to be easily removed by centrifugation. Sample C, with the anion added first, showed a 46% reduction in turbidity as compared to the untreated sample, indicating that the precipitate that formed was large enough to be easily spun out by centrifugation. The turbidity reduction also indicates that some amount of cellular debris and/or colloidal material was bound up by the precipitate and removed in the pellet.

Example 3

A pilot-scale experiment using calcium and phosphate as precipitants and the effects on downstream clarification and chromatography steps: A mAb, anti-AB #1, was produced by recombinant CHO cells cultured in serum free media in a 500 L bioreactor. At the time of harvest, the culture was brought to room temperature (18-25° C.). 350 L of the culture was left untreated and served as a negative control. 150 L of the culture was transferred to a 200 L carboy and slowly mixed with an overhead mixer. A buffer was added to 40 mM to control the pH. 2M potassium phosphate was then added to a concentration of 20 mM. 5M calcium chloride was then added to a concentration of 30 mM. The pH of the mixture was 7.3. The flocculated culture was incubated for 160 minutes while mixing. At the end of the incubation the pH of mixture was 7.0.

Both the flocculated and untreated cultures were processed through an Alfa Laval BTPX 205 disc stack centrifuge at a flow rate of 4.4 L/min and a bowl speed of 7630 RPM (8000 g). The steady state centrate turbidity of the flocculated sample was 14 NTU, as compared to 117 NTU for the untreated sample, an 88% reduction in turbidity. The recovery of antibody titer in the flocculated centrate was 96% as compared to the untreated centrate. The level of host cell proteins (HCP) in the flocculated centrate was reduced by 35% from 533,341 ppm to 348,087 ppm as compared to the untreated centrate.

Both the flocculated and untreated centrates were processed through Millipore A1HC Pad Filters to a capacity of 250 L of centrate per square meter of filter. The untreated sample showed a steadily increasing breakthrough of turbidity, from 4 NTU at 24 L/m$^2$ to 26 NTU at 121 L/m$^2$ to 37 NTU at 254 L/m$^2$. The final pad filtrate pool turbidity for the untreated sample was 21 NTU. The flocculated sample showed only a small rise in turbidity through the pads, from 2 NTU at 21 L/m$^2$ to 6 NTU at 150 L/m$^2$ to 7 NTU at 254 L/m$^2$. The final pad filtrate pool turbidity for the flocculated sample was 5 NTU, a 76% reduction in turbidity as compared to the untreated sample.

After pad filtration and additional filtration through a 0.2 µm polishing filter, the samples were chromatographed using a GE Healthcare MabSelect Protein A affinity column. When antibodies are eluted from Protein A columns, the peak pools often are turbid, and that turbidity typically increases when the peak is neutralized. The untreated peak pool had a turbidity of 10 NTU, and increased to 22 NTU upon neutralization. The flocculated peak pool had a turbidity of 3 NTU, and increased to 8 NTU upon neutralization, 63% lower than the untreated peak.

Example 4

Flocculation with calcium and phosphate resulting in reduced turbidity in both the clarified conditioned media and in the Protein A peak. Significant reduction of both a cell-related and a product-related impurity were also achieved.

A mAb, anti-5T4, was produced by recombinant CHO cells cultured in serum free media. Approximately 3 L of culture was left untreated and served as a negative control. Another 3 L of the culture was transferred to a 4 L vessel. A buffer was added to 40 mM to control the pH and gently mixed at 18-24° C. 2M potassium phosphate was then added to a concentration of 20 mM and the solution gently mixed. 5M calcium chloride was then added to a concentration of 30 mM and the solution gently mixed. The pH of the mixture was 7.2. The flocculated culture was transferred to three 2 L Erlenmeyer flasks and incubated for 2 hours while mixing. At the end of the incubation the pH of mixture was 7.0.

A 50 mL sample of both the flocculated culture and the untreated culture were spun at 340 g for ten minutes. The clarified supernatant was removed and assayed for antibody concentration by Protein A HPLC, and for turbidity using a nephalometer. The total recovery of product-related material was 78% as compared to the untreated sample. The turbidity of the untreated sample was 29 NTU. The turbidity of the flocculated sample was 2 NTU, a 93% reduction in turbidity as compared to the untreated sample.

Both the flocculated and untreated samples were processed through Millipore A1HC Pad Filters. After pad filtration and additional filtration through a 0.2 µm polishing filter, the samples were chromatographed using a GE Healthcare MabSelect Protein A affinity column. As antibodies elute from Protein A columns at high concentrations, the material in the apex of the product peak often precipitates, resulting in a turbid solution. The level of precipitation in the peak apex of the untreated sample, as measured by absorbance at 600 nm in a spectrophotometer, was 1.85 AU. The level of precipitation in the peak apex of the flocculated sample, as measured by absorbance at 600 nm in a spectrophotometer, was 0.03 AU, a 98% reduction in turbidity as compared to the untreated sample.

When antibodies are eluted from Protein A columns, the peak pools are occasionally turbid. Upon neutralization, the turbidity typically increases significantly between pH 5.5 and pH 6.0, as material precipitates and falls out of solution. Some of this precipitate tends to become soluble again as the pH is raised above 7. The untreated peak pool, with an antibody concentration of 8.1 mg/mL had a turbidity of 8.5 NTU when eluted, increased to 839 NTU between pH 5.5 and 6.0, and decreased to 53 NTU at pH 7.0. Upon filtration through a 0.2 µm sterilizing grade filter, the turbidity was only reduced to 40 NTU.

The flocculated product pool eluted from the column in less volume and therefore was more concentrated. The flocculated peak pool, with an antibody concentration of 15.1 mg/mL had a turbidity of 5.6 NTU when eluted, increased to 31 NTU between pH 5.5 and 6.0, a 96% reduction in turbidity from the control. The turbidity increased slightly to 46 NTU at pH 7.0 at 15.1 mg/mL. Upon filtration through a 0.2 µm sterilizing grade filter, the turbidity was reduced to 8.1 NTU, a reduction of 80% from the control.

When the neutralized Protein A peak was diluted to a concentration of 8.1 mg/mL to match the untreated sample, the turbidity of the unfiltered flocculated sample decreased from 46 NTU to 25 NTU, a 53% reduction as compared to the untreated sample. Upon filtration through a 0.2 µm sterilizing grade filter, the turbidity was reduced to 4.1 NTU, a 90% reduction in turbidity as compared to the untreated sample.

The level of high molecular weight (HMW) aggregate present in the Protein A peak pool was measured by Size-Exclusion HPLC. The level of aggregate in the untreated sample was 9.51%. The level of aggregate in the flocculated sample was 1.05%, an 89% reduction in aggregate as compared to the untreated sample. With the reduction in aggregate taken into account, the 78% product recovery in the culture translates to an 85% recovery of the desired monomer.

The levels of host cell proteins (HCP), unwanted impurities secreted by the CHO cells, were measured at different steps of the process using an ELISA. The HCP levels are reported as parts per million (ppm), equivalent to ng of HCP per mg of antibody. The HCP level in the untreated culture was 2.53E6 ppm. The HCP level in the flocculated conditioned medium was 3.83E5 ppm, an 84% reduction from the untreated culture. Both the untreated and flocculated cultures had an approximately 60% reduction in HCP through the pad filters to 1.02E6 and 1.62E5 respectively. Upon purification over the Protein A column, the levels of HCP in the untreated sample were reduced by 90% to 1.03E5 ppm. The levels of HCP in the flocculated sample were reduced by 98% to 3.83E2 ppm. Overall, there was a 1.4 log removal of HCP for the untreated purification train. The flocculated purification train achieved a 3.8 log removal of HCP resulting in a 250-fold reduction in HCP as compared to the untreated purification train.

While a number of implementations have been described, the invention is not so limited.

As an example, in some implementations, the flocculation methods described herein can be performed without cells present, for example, after the cells have been removed. The medium may contain non-cellular insoluble material (see Example 5 below).

Example 5

The use of calcium and phosphate to form a solid precipitate to aid in filtration of a turbid protein-containing solution: A mAb, anti-GDF8 #1, was produced by recombinant CHO cells cultured in serum free media. The cells were removed by an Alfa Laval BTPX 205 disc stack centrifuge and the resulting centrate was processed through Millipore A1HC Pad Filters. After pad filtration and additional filtration through a 0.2 µm polishing filter, the samples were chromatographed using a GE Healthcare MabSelect Protein A affinity column. When antibodies are eluted from Protein A columns, using a low pH buffer, the peak pools are occasionally turbid. Upon neutralization, the turbidity typically increases significantly.

In this example, the Protein A peak was held unfiltered for 7 days at 4° C. and then warmed up to room temperature. The turbidity of the peak was 192 NTU. The peak was split into two 800 mL samples, with one sample left untreated. To the second sample was added 4 mM potassium phosphate and 6 mM calcium chloride. The treated sample was then shaken in a 2 L Erlenmeyer flask for 1 hour at 18-25° C. After shaking the turbidity of the treated sample was 460 NTU.

Both the untreated and treated samples were then filtered through 17.7 cm$^2$ Millipore Express SHC 0.5/0.2 µm polyethersulfone capsule filters. Based on the amount of solution that was able to pass through each filter, a maximum filter capacity was calculated. The maximum filter capacity is the number of liters of solution that can pass through 1 m$^2$ of filter before the filter will plug and no more solution can pass. The untreated sample was able to achieve a maximum filter capacity of approximately 30 L/m$^2$ while the treated sample achieved a maximum filter capacity of approximately 1500 L/m$^2$, a 50-fold increase in filter capacity. The post-filter turbidity for both the untreated and treated samples was 9 NTU, indicating that the treatment did not likely result in the removal of additional particulate matter, but did serve as a filter-aid and allowed larger volumes of solution to pass through the filter before it plugged.

Example 6

The effect of scale and mixing method on the use of calcium and phosphate to form a solid precipitate to aid in the removal of particulate matter in a turbid protein-containing solution: Anti-AB #2 mAb, noted as "mAb B" in FIGS. 2 and 3, was produced by recombinant CHO cells cultured in serum free media in pilot scale bioreactors (160-500 L cell culture). Approximately 125 L, 1.5 L or 50 mL of the cell-containing conditioned media was aliquoted in to a 200 L carboy, a 2 L beaker, or a 125 mL Erlenmeyer flask, respectively. HEPES was added to 40 mM to control the pH. The 200 L carboy and the 2 L beaker were mixed with impellers. The 125 mL Erlenmeyer was mixed by a shaker. A concentrated solution of potassium phosphate was added to each mixture to achieve a final concentration of 20 mM in the final solution. A concentrated solution of calcium chloride was added to each solution to achieve a final target concentration of 30 mM and mixed. The final pHs were between 7.0 and 7.5. The solid and medium were incubated for greater than one hour under mixing conditions at room temperature (20-23° C.). 50 mL aliquots of an untreated sample, and the 125 L, 1.5 L, and 50 mL treated samples were centrifuged for 10 minutes at 340×g. The turbidities and antibody concentrations in the supernatants were measured.

Figure 2:
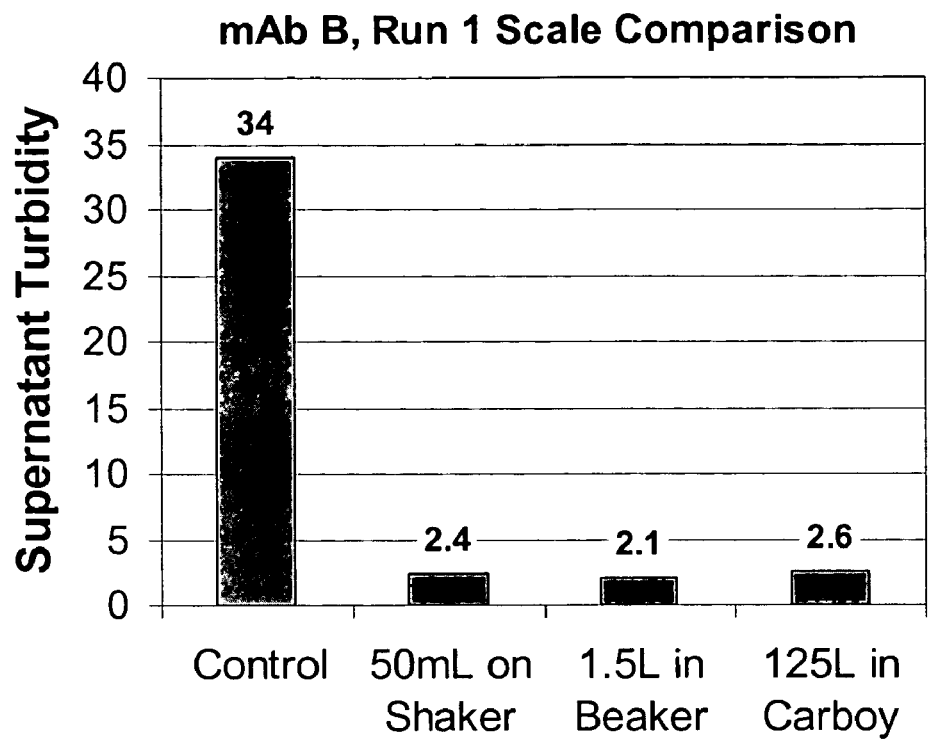
FIG. 2 is a graphical representation that shows the effect of scale and mixing method on flocculation.

The effect on turbidity of the scale and method of mixing is shown in FIG. 2. The turbidity is reduced by more than 90% from the control in all of the flocculation examples independent of scale and independent of mixing method (impeller or shaker). Additionally, the antibody recovery in all treated samples was 100% as compared to the untreated sample. Thus, it does not appear that flocculation in the present invention is dependent upon scale or upon mixing method for these widely different conditions.

The levels of host cell proteins (HCP), unwanted impurities secreted by the CHO cells, were measured in the untreated supernatant and the treated 125 L sample using an ELISA. The HCP levels are reported as parts per million (ppm), equivalent to ng of HCP per mg of antibody. The treated 125 L sample had a reduction in HCP of 50% as compared to the untreated sample.

Example 7

Figure 3:
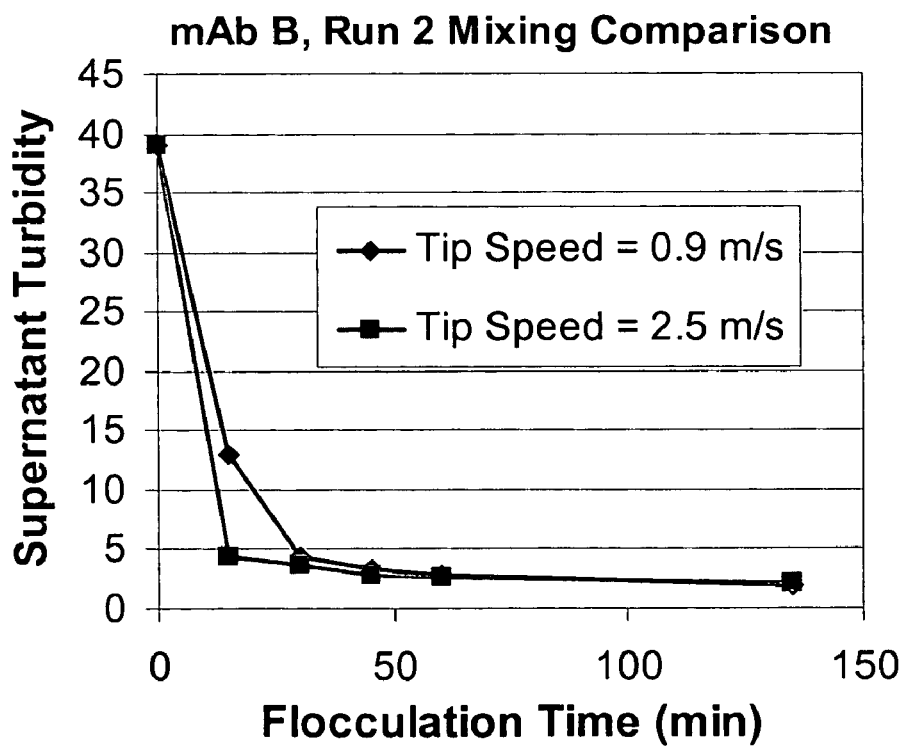
FIG. 3 is a graphical representation that shows the effect of mixing speed on flocculation.

The effect of mixing speed on the use of calcium and phosphate to form a solid precipitate to aid in the removal of particulate matter in a turbid protein-containing solution: Anti-AB #2 mAb, noted as "mAb B" in FIG. 3, was produced by recombinant CHO cells cultured in serum free media in pilot scale bioreactors (160-500 L cell culture). Approximately 125 L of the cell-containing conditioned media was placed in to two 200 L carboys. HEPES was added to 40 mM to control the pH. The mixing was performed with impellers, one operated at a tip speed of 0.9 m/s and the other at 2.5 m/s. A concentrated solution of potassium phosphate was added to the mixture to achieve a final concentration of 20 mM in the final solution. A concentrated solution of calcium chloride was added to the solution to achieve a final target concentration of 30 mM and mixed. The final pH was between 7.0 and 7.5. The solid and medium were incubated under mixing conditions at room temperature (20-23° C.), and samples were taken at various time points. The turbidity of each sample supernatant was measured after centrifuging at 340×g for ten minutes. The effect on turbidity of the impeller tip speed is shown in FIG. 3. The turbidity is reduced by more than 90% from the control in all of the flocculation examples independent of the tip speeds investigated after one hour. The faster tip speed appeared to have a faster reduction in turbidity at the 15 minute time point. This difference is, however, not significant. Thus, it does not appear that flocculation in the present invention is dependent upon tip speed for the speeds investigated after one hour of incubation.

The levels of host cell proteins (HCP), unwanted impurities produced by the CHO cells, were measured in the untreated supernatant and the treated 0.9 m/s sample using an ELISA. The HCP levels are reported as parts per million (ppm), equivalent to ng of HCP per mg of antibody. The treated sample had a reduction in HCP of 47% as compared to the untreated sample.

Example 8

Large Scale Flocculation

Figure 4:
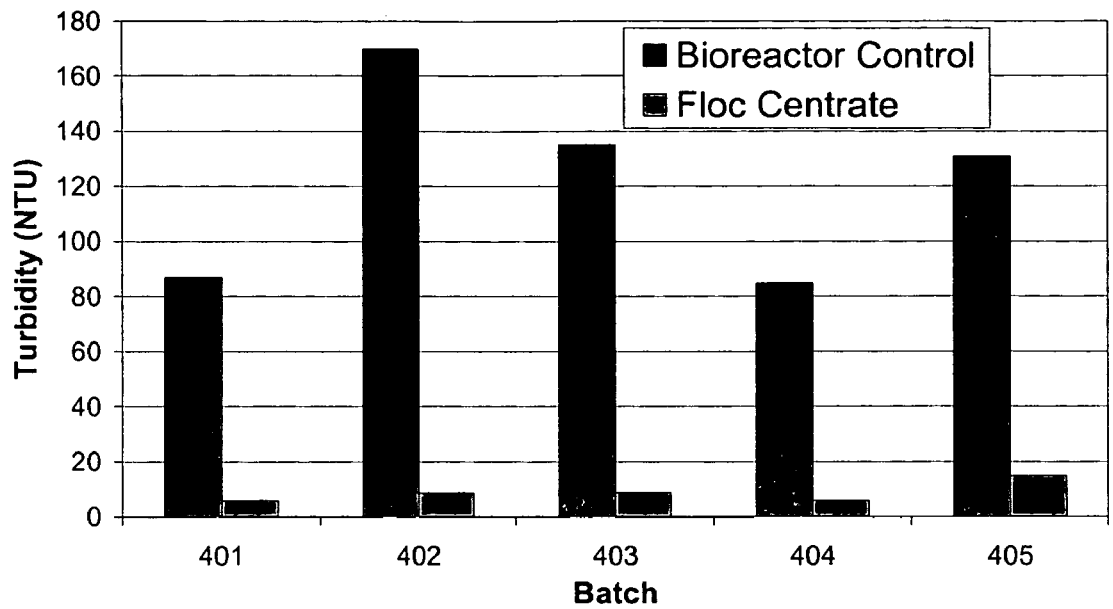
FIG. 4 is a graphical summary of five pilot scale flocculation experiments.

A pilot-scale experiment using calcium and phosphate as precipitants and the effects on downstream clarification and chromatography steps: A mAb, anti-IL-13 #1 (noted as mAb E in FIGS. 4 and 5), was produced in five different batches by recombinant CHO cells cultured in serum free media in a 190 L bioreactor. The bioreactor was run with a 12-14 day culture time, and the cells had a viability between $8 \times 10^6$-$11 \times 10^6$ viable cells/mL, and were 66-88% viable. At the time of harvest, the culture was brought to room temperature (18-25° C.). 150 L of the culture was transferred to a 200 L carboy (for the first four batches) or left in the bioreactor (for the last batch) and slowly mixed with an overhead mixer. HEPES buffer was added to 40 mM to control the pH. 2M potassium phosphate was then added to a concentration of 20 mM. 5M calcium chloride was then added to a concentration of 30 mM. The pH of the mixture was between 7 and 7.5. The flocculated culture was incubated for between 2 and 3 hours while mixing.

Figure 5:
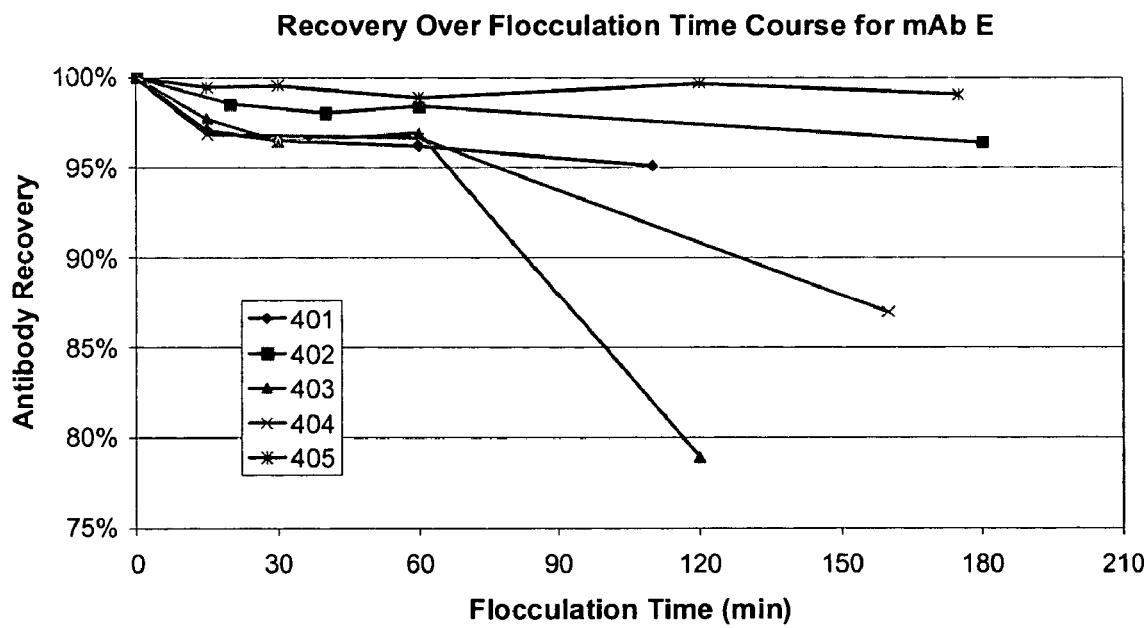
FIG. 5 is a graphical summary that shows changes in % antibody recovery over time for each of the five pilot scale flocculation experiments summarized in FIG. 4.

The flocculated cultures were processed through an Alfa Laval BTPX 205 disc stack centrifuge at a flow rate between 4 and 5 L/min and a bowl speed of 7630 RPM (8000 g). The turbidity of the centrates obtained are compared to the supernatant of the unflocculated sample (obtained from the centrifugation of the untreated control at 340 g for ten minutes) in FIG. 4. In all cases, the flocculation reduces the turbidity by greater than 85%. The recovery of antibody titer in the flocculated supernatants is shown in FIG. 5 as a function of incubation time, and is above 75% in all cases. 50 mL samples were taken from batches 403 and 405 and incubated in 125 mL Erlenmeyer flasks for additional time. After 7 hours, batch 403 had a titer of 60% of the untreated sample, and batch 405 had a titer of 80% of the untreated sample.

The levels of host cell proteins (HCP), unwanted impurities secreted by the CHO cells, were measured in the untreated supernatants and treated centrates using an ELISA. The HCP levels are reported as parts per million (ppm), equivalent to ng of HCP per mg of antibody. The treated samples from the 5 batches showed reductions in HCP from 49%-69% as compared to the untreated samples.

The first 3 batches were processed through Millipore A1HC Pad Filters to a capacity of 270 L of centrate per square meter of filter at a flux of 120 liters per square meter per hour with no rise in pressure or turbidity.

After pad filtration, the samples generally remained stable for many days as measured by turbidity.

The last 2 batches went directly over 0.2 µm filters without going through pads. Filter capacities of 730 and 160 L/m$^2$ were achieved, respectively, without the use of pad filters prior to the 0.2 µm filters. These filter capacities represent a significant improvement in filterability over that of unflocculated material. Upon holding the 0.2 µm-filtered centrates (without pads) at room temperature (18-24° C.), the turbidity begins to increase within a few hours due to continued precipitation of the calcium and phosphate. After 24-48 hours the precipitate settles, forming a crystalline layer of calcium phosphate at the bottom of the container. The resulting clarified protein containing solution has excellent filterability characteristics both before and after the precipitate settles. No antibody is lost in the precipitate.

Flocculation for the final batch was performed directly in the pilot bioreactor. The reactor was effectively cleaned using standard clean-in-place (CIP) procedures (water rinse followed by a 0.1N NaOH wash at 60-80° C.)

All 5 batches were processed at pilot scale through a Protein A column, anion exchange step, virus retaining filter, and final ultrafiltration/diafiltration (UF/DF) with no operational issues. Neutralized Protein A peaks all had turbidities of <20 NTU and were highly filterable. Product quality, such as levels of high molecular weight aggregate and low molecular weight clips, as measured by size exclusion HPLC and SDS-PAGE gel electrophoresis, and levels of acidic and basic species, as measured by cation exchange HPLC, were comparable to a previous non-flocculated pilot campaign with this antibody.

Example 9

The use of calcium and phosphate as precipitants and the effects on a downstream Protein A chromatography step and subsequent filtration: Three mAbs, anti-AB #2, anti-GDF8 #1, and anti-IL22 were produced by recombinant CHO cells cultured in serum free media. For each, the cultures were split in half, with the first sample being left untreated. To the second sample (the treated sample) was added HEPES to a level of 40 mM, potassium phosphate to a level of 20 mM, and calcium chloride to a level of 30 mM. The cells from all samples were removed by centrifugation and the resulting supernatants were processed through Millipore A1HC Pad Filters. After pad filtration and additional filtration through 0.2 µm polishing filters, the samples were chromatographed using GE Healthcare MabSelect Protein A affinity columns. When antibodies are eluted from Protein A columns, using a low pH buffer, the peak pools are occasionally turbid. Upon neutralization, the turbidity typically increases significantly.

The neutralized peak turbidities of the untreated and treated samples are shown in Table 2 below. All three treated samples showed a significant reduction in neutralized peak turbidity as compared to the untreated samples.

TABLE 2

Decrease in Protein A Peak turbidity after calcium phosphate treatment of cell culture prior to loading

| | Peak Turbidity of Untreated Sample (NTU) | Peak Turbidity of Treated Sample (NTU) | % Reduction in Turbidity from Untreated to Treated Sample |
|---|---|---|---|
| anti-AB #2 | 61 | 25 | 60% |
| anti-GDF8 #1 | 153 | 25 | 84% |
| anti-IL22 | 233 | 12 | 95% |

Both the untreated and treated anti-IL22 neutralized peaks were then filtered through 2.8 cm$^2$ Pall Acrodisc Supor 0.8/0.2 µm polyethersulfone syringe filters. Based on the amount of solution that was able to pass through each filter, a maximum filter capacity was calculated. The maximum filter capacity is the number of liters of solution that can pass through 1 m$^2$ of filter before the filter will plug and no more solution can pass. The untreated sample was able to achieve a maximum filter capacity of approximately 10-30 L/m$^2$. 170 L/m$^2$ of the treated sample passed through the filter without a reduction in flow, at which point no treated sample remained. The treated sample passed through the filter too rapidly to accurately calculate a maximum filter capacity. However, as there was no reduction in flow out to a challenge of 170 L/m$^2$, it can be assumed that the maximum capacity would have been significantly greater than 170 L/m$^2$.

All publications, patent applications, patents, and other references mentioned herein are incorporated by reference herein in their entirety.

Other embodiments are within the scope of the following claims.

What is claimed is:

1. A method for separating a solid from a target protein, comprising:
   forming a solid comprising a first cation, a first anion and an impurity in a medium comprising the target protein; and separating the solid from the target protein, wherein at least about 50% of the target protein in the medium is separated and wherein the medium is clarified after the separation and further wherein the impurity is at least one of a host cell, host cell protein, DNA or cellular debris;

wherein the solubility product constant of a salt consisting of the first cation and first anion is no more than about $10^{-4} M^2$;

provided the first cation is not aluminum or iron.

2. The method of claim 1, wherein the first cation is selected from the group consisting of calcium, magnesium, strontium, scandium, lanthanum, silicon, titanium, zirconium, thorium, manganese, cobalt, copper, chromium, nickel, zinc, and vanadium.

3. The method of claim 2, wherein the first cation is calcium.

4. The method of claim 1, wherein the first anion is selected from the group consisting of phosphate, carbonate, chromate, tungstate, hydroxide, halide, succinate, tartrate, citrate, sulfite, molybdate, nitrate, fluoride, silicate, and alginate.

5. The method of claim 4, wherein the first anion is phosphate.

6. The method of claim 1, wherein the first cation is calcium, and the first anion is phosphate.

7. The method of claim 1, further comprising introducing from about 4 mM to about 200 mM of the first cation or the first anion into the medium.

8. The method of claim 1, wherein the product of the concentrations of the first cation and the first anion before forming the solid is greater than about $10^{-5} M^2$.

9. The method of claim 8, wherein the product of the concentrations of the first cation and the first anion before forming the solid is greater than about $10^{-4} M^2$.

10. The method of claim 9, wherein the product of the concentrations of the first cation and the first anion before forming the solid is greater than about $2.7 \times 10^{-2} M^2$.

11. The method of claim 1, wherein the concentrations of the first cation and the first anion in the medium are different.

12. The method of claim 1, wherein the concentrations of the first cation and the first anion in the medium are the same.

13. The method of claim 1, further comprising changing the pH of the medium.

14. The method of claim 1, wherein the pH of the medium is maintained between about 5 to about 9.

15. The method of claim 1, wherein at least about 70% of the target protein in the medium is separated.

16. The method of claim 1 wherein turbidity of the clarified medium is decreased by at least about 30% relative to a second clarified medium identical to the medium and free of the solid.

17. The method of claim 16, wherein the turbidity of the clarified medium is decreased by at least about 50%.

18. The method of claim 1, wherein the medium further comprises mammalian cells.

19. The method of claim 1, wherein the medium further comprises eukaryotic cells.

20. The method of claim 1, wherein the separation step comprises centrifuging the medium, filtering the medium through a microfiltration membrane, or filtering the medium through a depth filter.

21. The method of claim 1, wherein the solid further comprises a second cation species or a second anion.

22. The method of claim 1, wherein the medium comprising the target protein, after the solid is formed and separated, is applied to a Protein A column and eluted to provide an eluted peak having a lower turbidity than a similarly eluted peak of a second medium identical to the first medium and free of formation of the solid.

23. The method of claim 1, wherein the medium comprising the target protein, after the solid is formed and separated, is applied to a Protein A column and eluted to provide an eluted peak having a lower soluble impurity level than an eluted peak of a second medium identical to the medium and free of formation of the solid.

24. A method for separating a solid from a target protein, comprising:

introducing a first cation and a first anion into a medium comprising the target protein and an impurity;

precipitating a solid comprising the first cation, the first anion and the impurity; and separating the solid from the target protein, wherein at least about 50% of the target protein in the medium is separated and wherein the medium is clarified after the separation and further wherein the impurity is at least one of a host cell, host cell protein, DNA or cellular debris;

wherein the solubility product constant of a salt consisting of the first cation and first anion is no more than about $10^{-4} M^2$;

provided the first cation is not aluminum or iron.

25. The method of claim 4, wherein the first cation and the first anion are introduced sequentially.

26. The method of claim 24, wherein the first cation and the first anion are introduced simultaneously.

27. The method of claim 24, wherein the first cation is selected from the group consisting of calcium, magnesium, strontium, scandium, lanthanum, silicon, titanium, zirconium, thorium, manganese, cobalt, copper, chromium, nickel, zinc, and vanadium.

28. The method of claim 24, wherein the first anion is selected from the group consisting of phosphate, carbonate, chromate, tungstate, hydroxide, succinate, tartrate, citrate, sulfite, molybdate, nitrate, fluoride, silicate, and alginate.

29. The method of claim 24, further comprising introducing from about 4 mM to about 200 mM of the first cation or the first anion into the medium.

30. The method of claim 24, wherein the product of the concentrations of the first cation and the first anion is greater than about $10^{-5} M^2$.

31. The method of claim 30, wherein the product of the concentrations of the first cation and the first anion is greater than about $10^{-4} M^2$.

32. The method of claim 31, wherein the product of the concentrations of the first cation and the first anion is greater than about $2.7 \times 10^{-2} M^2$.

33. The method of claim 24, comprising introducing different concentrations of the first cation and the first anion into the medium.

34. The method of claim 24, comprising introducing the same concentration of the first cation and the first anion into the medium.

35. The method of claim 24, further comprising changing the pH of the medium.

36. The method of claim 24, wherein the pH of the medium is maintained between about 5 to about 9.

37. The method of claim 24, further comprising adjusting the temperature of the medium.

38. The method of claim 24, wherein at least about 70% of the target protein in the medium is separated.

39. The method of claim 24, wherein turbidity of the clarified medium is decreased by at least about 30% relative to a second clarified medium identical to the medium and free of the solid.

40. The method of claim 39, wherein the turbidity of the clarified medium is decreased by at least about 50%.

41. The method of claim 24, wherein the medium further comprises mammalian cells.

42. The method of claim 24, wherein the medium further comprises eukaryotic cells.

43. The method of claim 24, wherein the separation step comprises centrifuging the medium, filtering the medium through a microfiltration membrane, or filtering the medium through a depth filter.

44. The method of claim 24, wherein the solid further comprises a second cation or a second anion.

45. The method of claim 24, wherein the medium comprising the target protein, after the solid is formed and separated, is applied to a Protein A column and eluted to provide an eluted peak having a lower turbidity than a similarly eluted peak of a second medium identical to the first medium and free of formation of the solid.

46. The method of claim 24, wherein the medium comprising the target protein, after the solid is formed and separated, is applied to a Protein A column and eluted to provide an eluted peak having a lower soluble impurity level than an eluted peak of a second medium identical to the medium and free of formation of the solid.

47. The method of claim 1, wherein the target protein is a secreted protein.

48. The method of claim 47, wherein the target protein is selected from the group consisting of an antibody, an antigen-binding fragment of an antibody, a soluble receptor, a receptor fusion, a cytokine, a growth factor, an enzyme, and a clotting factor.

49. The method of claim 48, wherein the target protein is an antibody or an antigen-binding fragment thereof.

50. The method of claim 49, wherein the antibody or antigen-binding fragment thereof binds to an Aβ peptide, interleukin-13, interleukin-22, 5T4, or growth differentiation factor-8.

51. The method of claim 24, wherein the target protein is a secreted protein.

52. The method of claim 51, wherein the target protein is selected from the group consisting of an antibody, an antigen-binding fragment of an antibody, a soluble receptor, a receptor fusion, a cytokine, a growth factor, an enzyme, and a clotting factor.

53. The method of claim 52, wherein the target protein is an antibody or an antigen-binding fragment thereof.

54. The method of claim 53, wherein the antibody or antigen-binding fragment thereof binds to an Aβ peptide, interleukin-13, interleukin-22, 5T4, or growth and differentiation factor-8.

55. A method, comprising: (i) forming a solid that includes a first cation and a first anion in a medium comprising a target protein and a turbidity-causing agent; and (ii) separating the solid and turbidity-causing agent from the solution by filtration, wherein at least about 50% of the target protein in the medium is separated, wherein the medium is clarified after the separation, wherein the turbidity-causing agent is at least one of a host cell, host cell protein, DNA or cellular debris; and wherein the solubility product constant of a salt consisting of the first cation and first anion is no more than about $10^{-4}M^2$;

provided the first cation is not aluminum or iron.

56. The method of claim 55, wherein the target moiety is a protein.

57. The method of claim 55, wherein the protein is a soluble protein.

58. The method of claim 27, wherein the first cation is calcium.

59. The method of claim 28, wherein the first anion is phosphate.

60. The method of claim 24, wherein the first cation is calcium, and the first anion is phosphate.

61. The method of claim 1, further comprising adjusting the temperature of the medium.

62. The method of claim 21, wherein the second cation is selected from the group consisting of calcium, magnesium, strontium, aluminum, scandium, lanthanum, silicon, titanium, zirconium, thorium, manganese, cobalt, copper, chromium, iron, nickel, zinc, and vanadium.

63. The method of claim 62, wherein the second cation is magnesium.

64. The method of claim 21, wherein the second anion is selected from the group consisting of phosphate, carbonate, chromate, tungstate, hydroxide, succinate, tartrate, citrate, sulfite, molybdate, nitrate, fluoride, silicate, and alginate.

65. The method of claim 64, wherein the second anion is carbonate.

66. The method of claim 44, wherein the second cation is selected from the group consisting of calcium, magnesium, strontium, aluminum, scandium, lanthanum, silicon, titanium, zirconium, thorium, manganese, cobalt, copper, chromium, iron, nickel, zinc, and vanadium.

67. The method of claim 66, wherein the second cation is magnesium.

68. The method of claim 1, wherein the impurity comprises DNA or a host cell protein.

69. The method of claim 24, wherein the impurity comprises DNA or a host cell protein.

* * * * *